(12) United States Patent
McFarlane

(10) Patent No.: US 7,390,316 B2
(45) Date of Patent: Jun. 24, 2008

(54) SEAL POSITIONING ASSEMBLY

(75) Inventor: Richard H. McFarlane, Singer Island, FL (US)

(73) Assignee: Teleflex Medical Incorporated, Limerick, PA (US)

( * ) Notice: Subject to any disclaimer, the term of this patent is extended or adjusted under 35 U.S.C. 154(b) by 0 days.

(21) Appl. No.: 10/914,053

(22) Filed: Aug. 6, 2004

(65) Prior Publication Data

US 2005/0113757 A1 May 26, 2005

Related U.S. Application Data

(60) Provisional application No. 60/493,673, filed on Aug. 8, 2003.

(51) Int. Cl.
*A61M 5/178* (2006.01)

(52) U.S. Cl. .................................................. 604/167.03

(58) Field of Classification Search ...............................
604/167.01–167.06, 256, 246, 539, 506,
604/164.12, 533, 536; 251/171, 149.1, 82;
606/180, 213, 185; 137/849
See application file for complete search history.

(56) References Cited

U.S. PATENT DOCUMENTS

| | | | |
|---|---|---|---|
| 4,426,062 A | 1/1984 | Bowron | |
| 4,931,042 A | 6/1990 | Holmes et al. | |
| 5,114,407 A | 5/1992 | Burbank | |
| 5,127,626 A | 7/1992 | Hilal et al. | |
| 5,156,596 A | 10/1992 | Balbierz et al. | |
| 5,224,952 A | 7/1993 | Deniega et al. | |
| 5,320,608 A | 6/1994 | Gerrone | |
| 5,350,364 A | 9/1994 | Stephens et al. | |
| 5,476,475 A | 12/1995 | Gadberry | |
| 5,492,304 A * | 2/1996 | Smith et al. | 251/149.1 |
| 5,501,674 A | 3/1996 | Trombley, III et al. | |
| 5,690,663 A | 11/1997 | Stephens | |
| 5,814,026 A | 9/1998 | Yoon | |
| 5,906,595 A | 5/1999 | Powell et al. | |
| 5,913,847 A | 6/1999 | Yoon | |
| 5,916,198 A | 6/1999 | Dillow | |
| 5,935,112 A * | 8/1999 | Stevens et al. | 604/256 |
| 5,989,233 A | 11/1999 | Yoon | |
| 6,039,748 A | 3/2000 | Savage et al. | |
| 6,077,249 A | 6/2000 | Dittrich et al. | |
| 6,083,203 A * | 7/2000 | Yoon | 604/167.01 |

(Continued)

FOREIGN PATENT DOCUMENTS

WO   WO 01/91834 A1   12/2001

*Primary Examiner*—Nicholas D. Lucchesi
*Assistant Examiner*—Christopher D Koharski
(74) *Attorney, Agent, or Firm*—Baker & Hostetler LLP

(57) ABSTRACT

An assembly structured to selectively orient a seal between an open position and a closed position. The assembly includes an expander structure disposable into a seal open or a seal closed orientation by being rotated or otherwise movable into and out of forced engagement with predetermined portions of the seal structure. The seal open orientation disposes the seal structure out of engagement with an instrument passing there through and may also facilitate a rapid venting of insufflation gas from an inflated body cavity, such as when the seal positioning assembly is used with a trocar assembly involved in the performance of laprascopic or like surgery. A biasing assembly may be connected to the seal structure to bias it in a normally closed position in the absence of an instrument disposed within the seal structure.

9 Claims, 20 Drawing Sheets

U.S. PATENT DOCUMENTS

| | | | |
|---|---|---|---|
| 6,093,176 A * | 7/2000 | Dennis | 604/256 |
| 6,692,467 B2 | 2/2004 | McFarlane | |
| 2001/0021825 A1 * | 9/2001 | Becker et al. | 604/167.01 |
| 2002/0072713 A1 * | 6/2002 | Almond et al. | 604/167.05 |

* cited by examiner

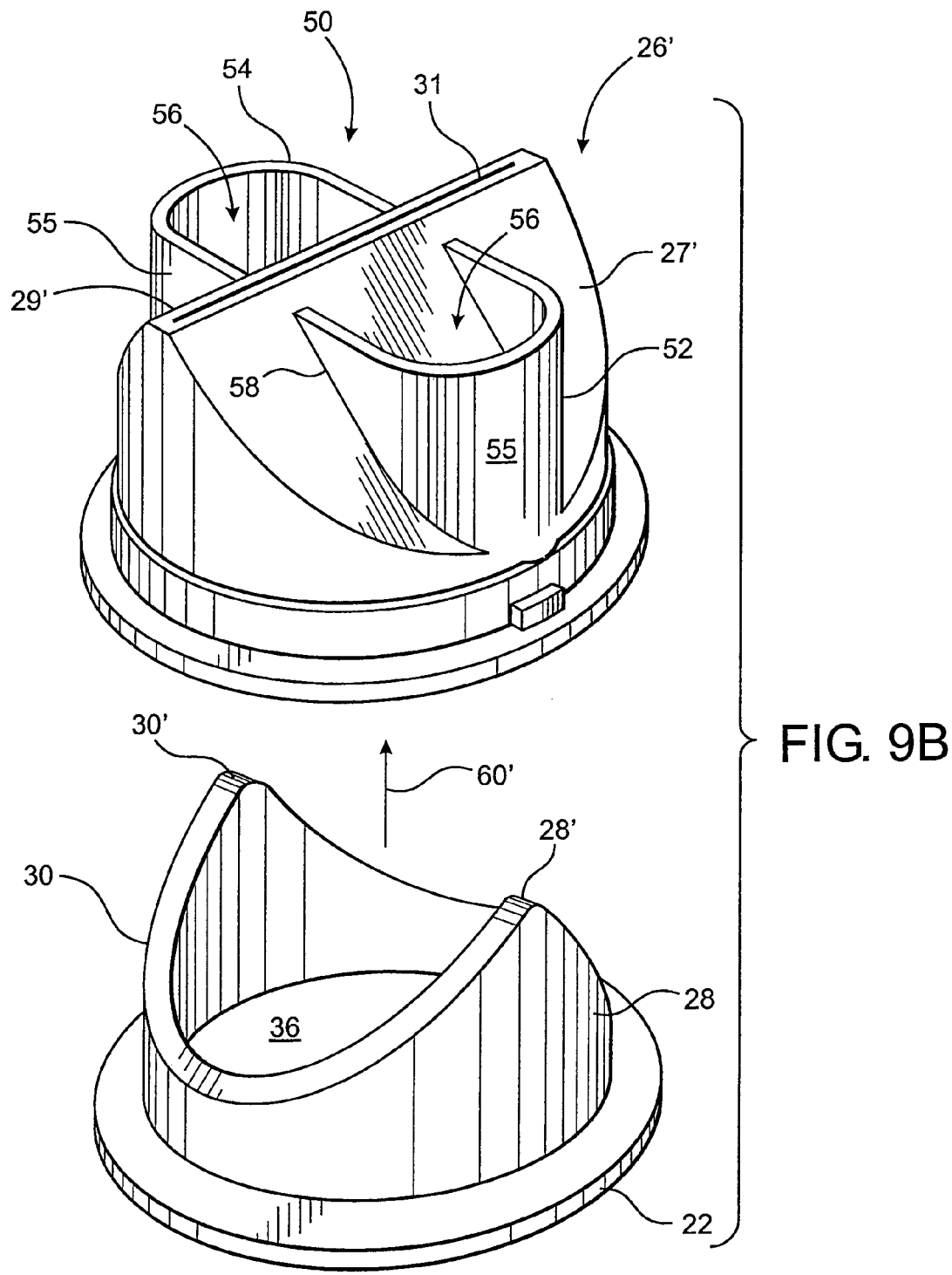

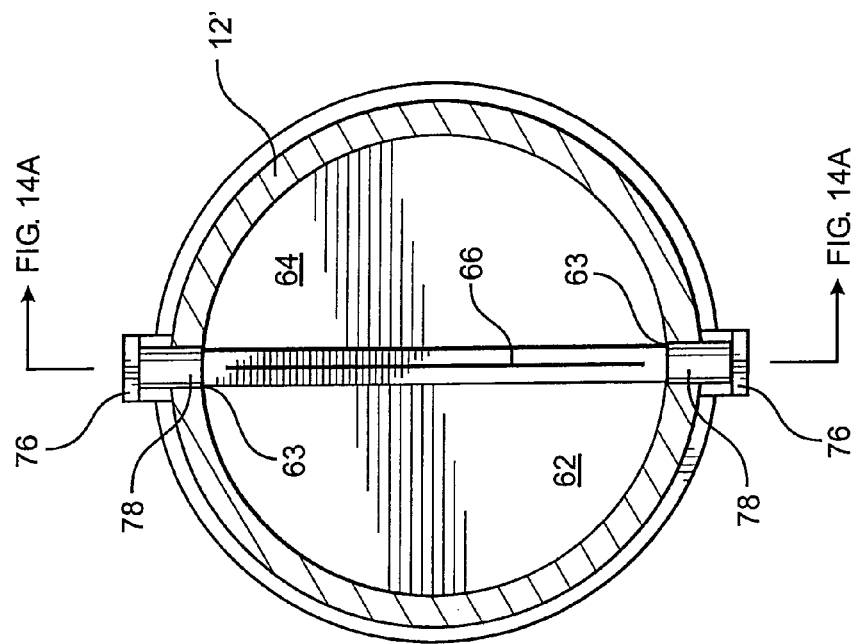
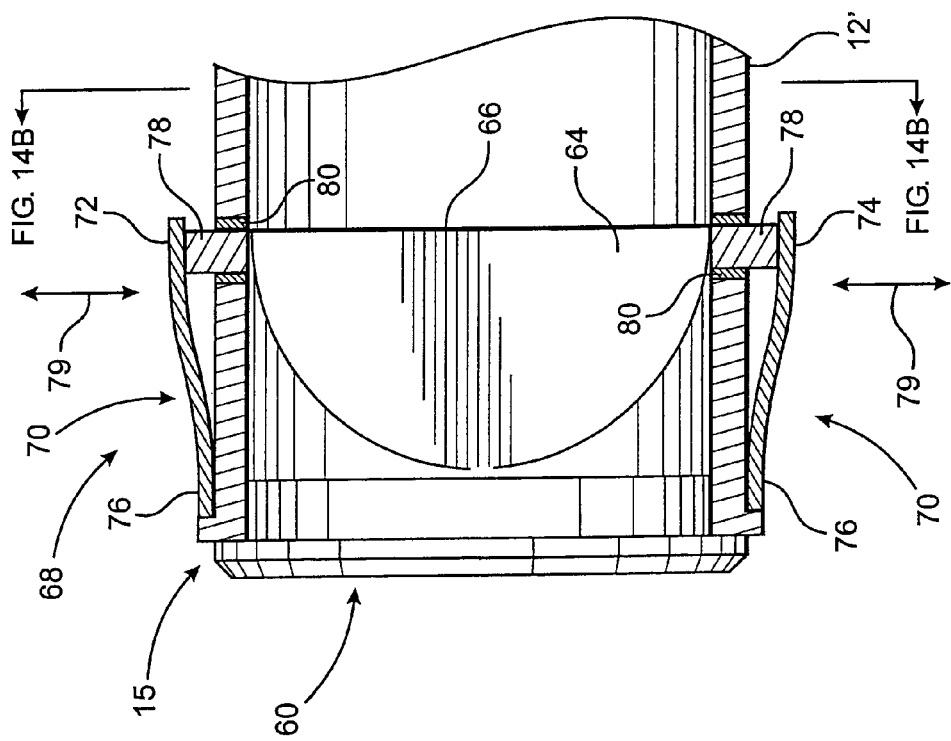

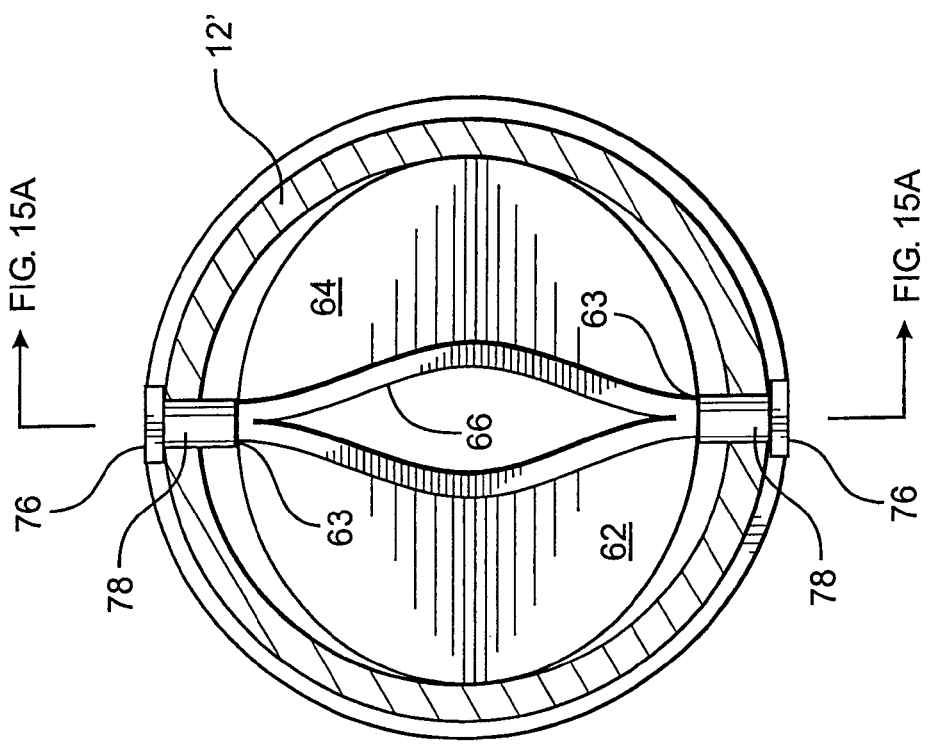
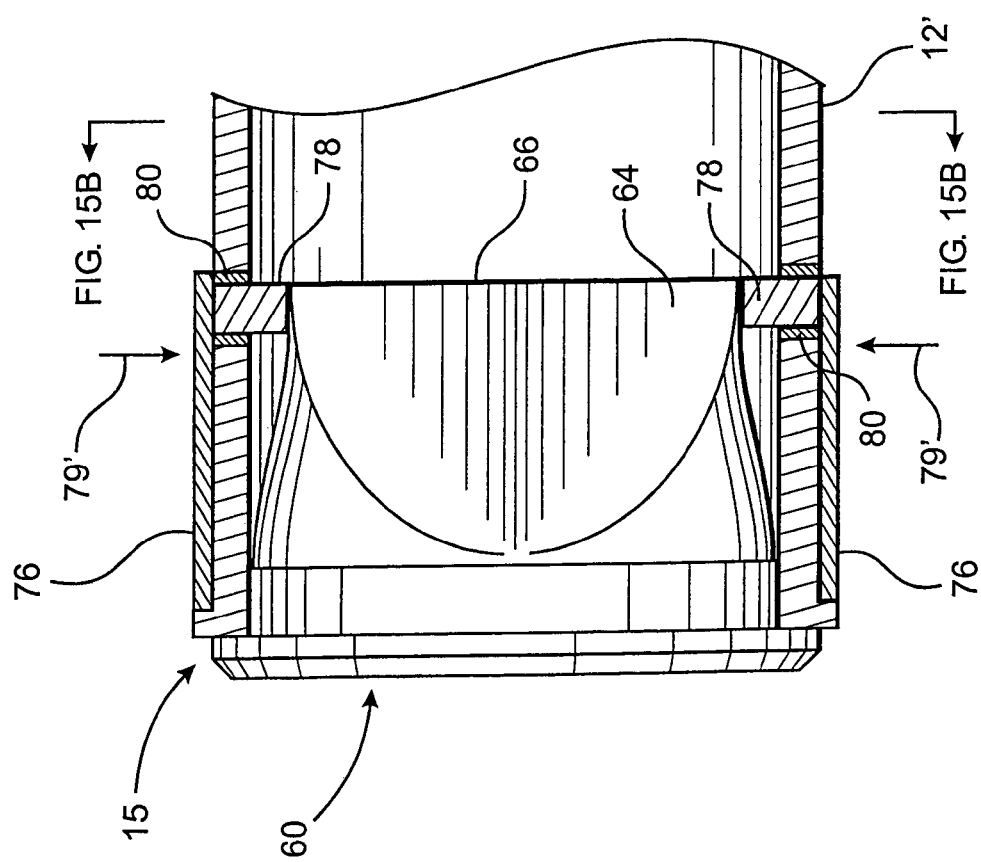

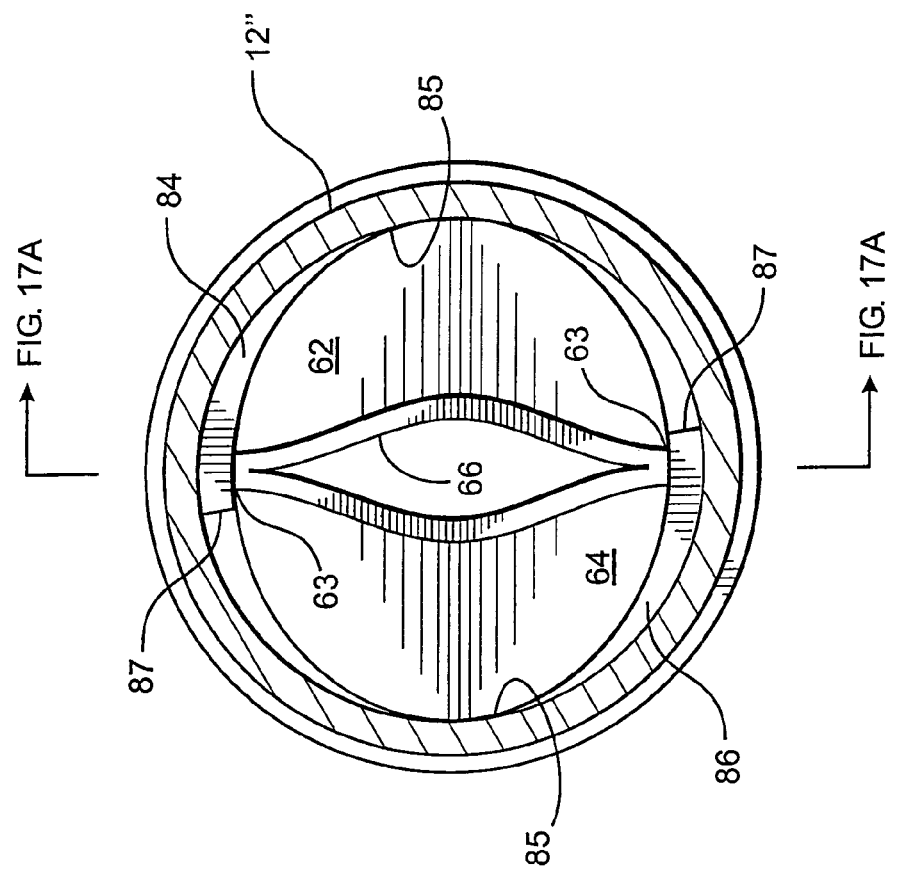
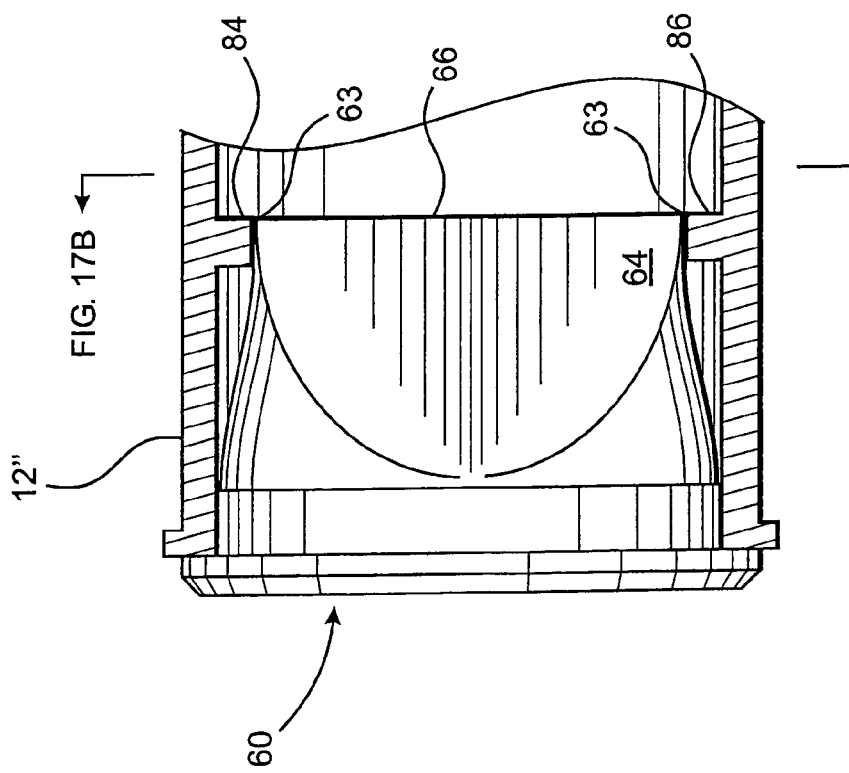

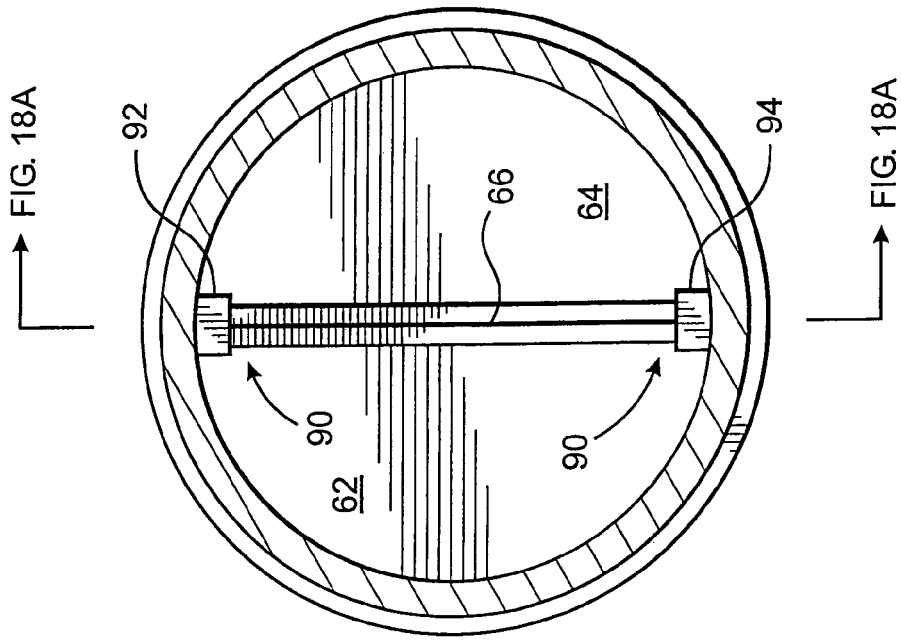
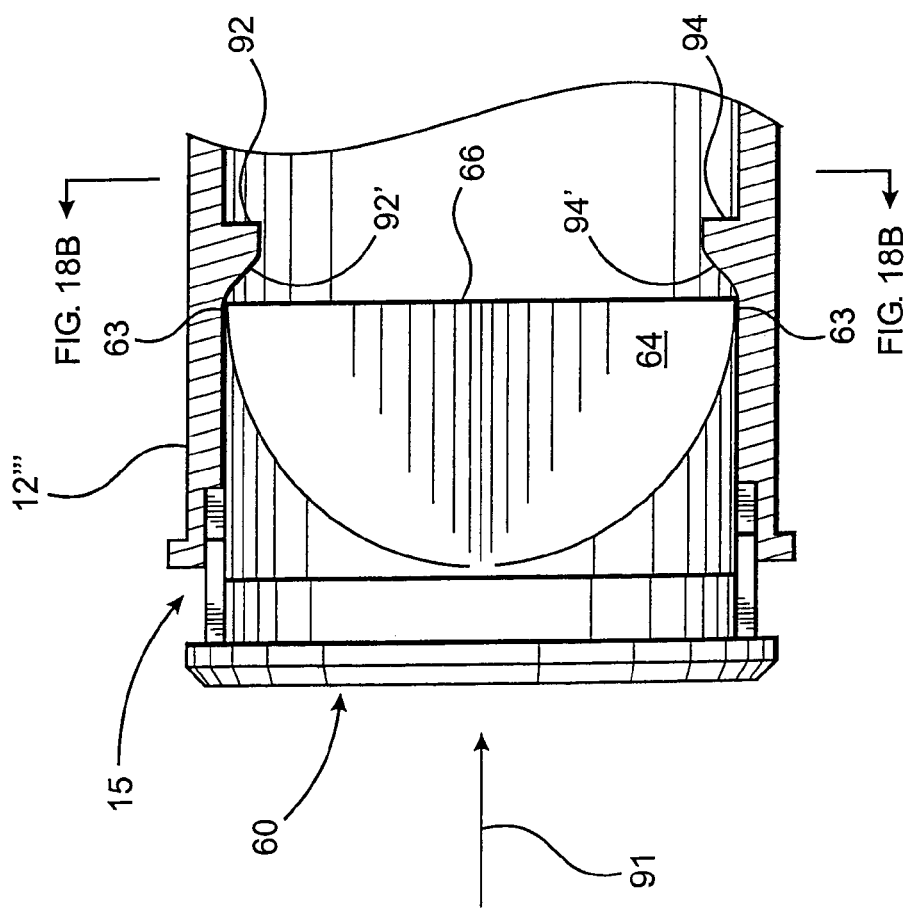

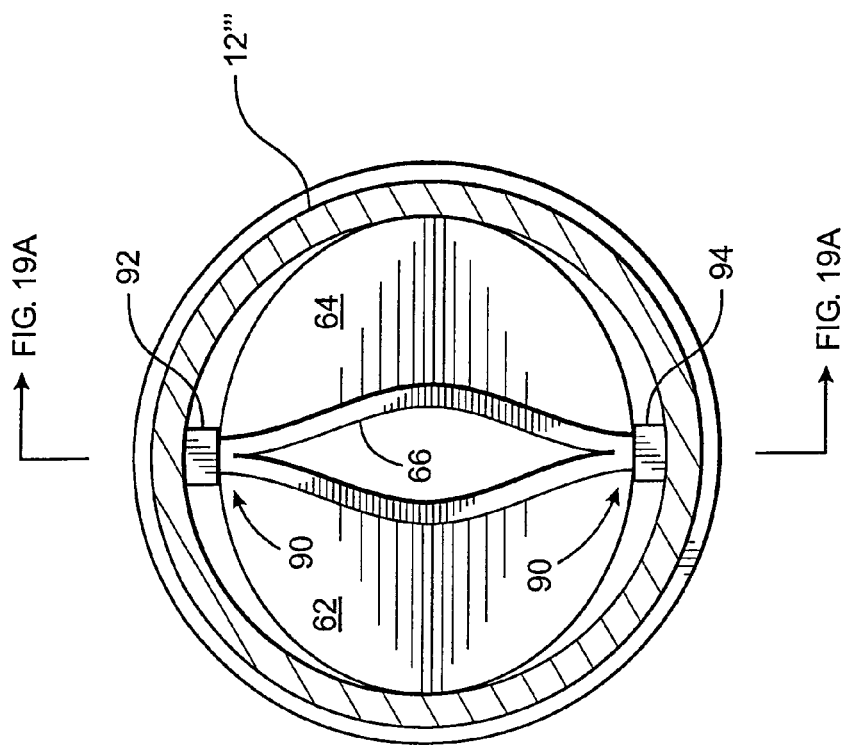
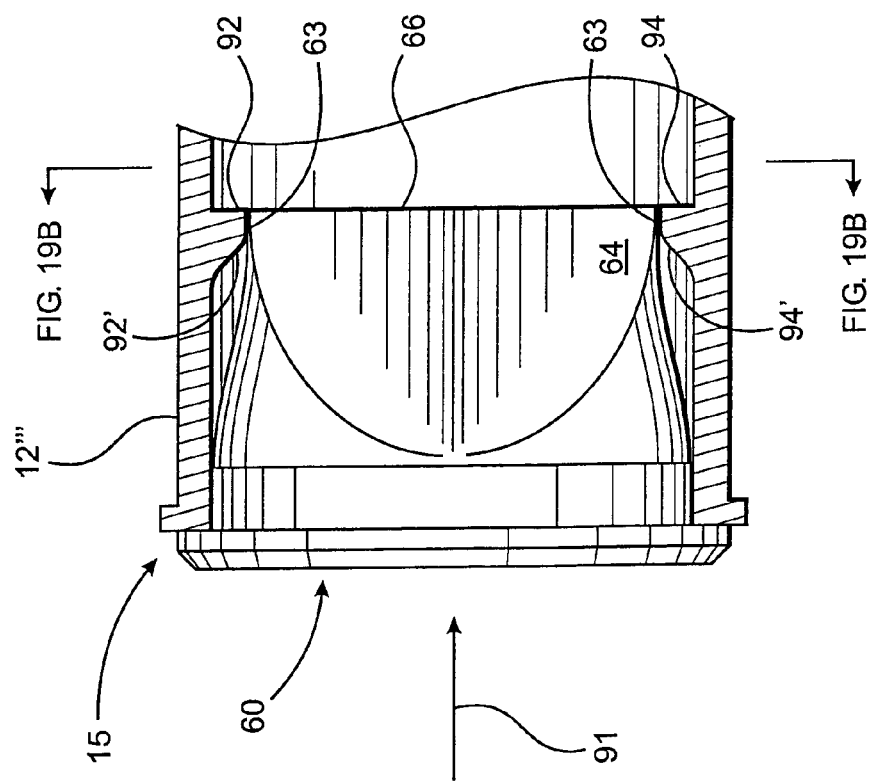

SEAL POSITIONING ASSEMBLY

CLAIM OF PRIORITY

The present application is based on and a claim to priority is made under 35 U.S.C. Section 119(e) to provisional patent application currently pending in the U.S. Patent and Trademark Office having Ser. No. 60/493,673 and a filing date of Aug. 8, 2003.

BACKGROUND OF THE INVENTION

1. Field of the Invention

The present invention is directed to a seal positioning assembly comprising an expander structure movable relative to a seal, that is primarily, but not exclusively, structured for use with a trocar assembly through which a medical instrument is passed during a surgical procedure. The expander structure is selectively positioned into a seal open orientation so as to dispose the seal substantially out of contact with a medical instrument or so as to accomplish rapid desufflation of a patient's inflated body cavity. In one or more preferred embodiments, the present invention may include a biasing assembly structured and disposed to bias the seal into a closed orientation when a medical instrument has been removed from or is otherwise not present within the trocar assembly.

2. Description of the Related Art

In recent years, the practice of laparoscopy for carrying out endoscopic surgical procedures has replaced major, invasive surgery in a variety of situations. Previously, routine surgical operations were performed by the physician making a large incision into an intended portion of a user's body in order to reach the targeted organ(s) and/or other body tissue. While the size of such major incisions would vary dependant upon the type of surgery needed, it was common-place for the incision to be extensive in order to provide adequate access to the interior body portions of the patient. Upon completion of the surgical procedure, the incision would be closed using conventional techniques. However, it was universally recognized that surgical procedures involving such extensive incisions resulted in significant trauma as well as prolonged recovery periods. In addition, the pain or discomfort endured by the patient, as well as the lack of mobility during such extended periods of recovery, were serious problems.

Because of such disadvantages, new procedures and instruments utilized with the aforementioned laprascopic and/or endoscopic surgery have continued to evolve, such that these new, less invasive surgical techniques have become common-place. In practice, one or more small openings are formed in the wall of the body cavity utilizing specifically designed penetrating instruments. Medical instruments designed to form the openings are structured to provide physical and visual access into the body cavity being treated. Representative medical instruments used in this type of surgery are generically referred to as a "trocar" or trocar assembly.

Typically, the trocar assembly includes a trocar body having a housing and an elongated sleeve or cannula defining an equally elongated channel or lumen on the interior thereof. In the initial formation of the entrance openings in the patient's body, an obturator is passed through the interior of the trocar by entering the housing portion at one end and passing along the entire length of the interior of the cannula. In most cases, the obturator includes a sharply pointed or appropriately structured tip which facilitates penetration of the exterior wall of the body cavity.

In order to assure that the medical personnel have adequate space for performing the intended surgical procedures, the body cavity is then typically inflated with an insufflation gas to maintain the cavity in a distended state. The insufflation gas is supplied through the interior of the trocar assembly by means of a gas inlet port associated therewith. In addition, the use of one or more valves or seals are provided within the housing portion of the trocar assembly for purposes of preventing the insufflation gas from escaping from the body cavity back through the interior of the trocar assembly. Maintaining the body cavity in an expanded or distended state is, of course, important to the efficient performance of many of the intended surgical procedures. Accordingly, various advancements have been made in the area of valves and seals associated with the trocar assembly in order to eliminate or significantly restrict the escape of the insufflation gas. Therefore, depending at least in part on the structure of the trocar, the type of instruments used in the laprascopic procedures and the intended surgical procedures to be performed, the structural modification of such valves and/or seals vary significantly from one another.

In spite of the availability of a wide variety of valve and/or seal structures, one commonly used structure incorporates what may be referred to as a "duckbill" configuration. The duckbill seal or valve typically comprises an interior channel through which an instrument passes while being inserted through and withdrawn from the interior of the trocar, relative to the body cavity involved in the surgical site. In addition, duckbill valves or seals normally are formed from a flexible material and include two or more converging flap structures having correspondingly disposed distal ends cooperatively positioned and collectively defining a valve opening, wherein the flap structures normally assume a closed position. The insertion of a medical instrument into the housing of the trocar assembly will result in the instrument passing axially through the duckbill valve and through the seal opening thereof by separating the distal ends of the converging flaps.

Further, when an instrument extends through the duckbill valve, the distal ends of the converging flap structures normally engage the outer surfaces of the instrument, but do not form a fluid tight seal therewith. However, one distinct advantage of using a duckbill valve or seal comprises its ability to prevent escape of insuflation gas from the body cavity, through the trocar, before a medical instrument has passed through the duckbill valve or after it has been removed there from. As set forth above, the converging flap structures of a duckbill valve are structured to normally assume a closed, sealed orientation when a medical instrument is absent there from. Therefore, if a medical instrument is not present in the trocar, insuflation gas passing into the trocar from the body cavity is normally prevented from escaping through the duckbill valve. Therefore, venting of the body cavity may typically occur by opening a stopcock or like venting structure on the trocar.

However, the extensive use of duckbill valves or seals has brought to light certain disadvantages associated therewith. These disadvantages include the existence of at least some frictional force exerted on the converging flap structures due to their sliding engagement with the instrument. These forces can tend to at least somewhat inhibit insertion or removal of the instrument and in some extreme cases, may cause the converging flaps to become inverted as the instrument is withdrawn from the interior of the trocar assembly. Another disadvantage involves the problem of the converging flaps of the duckbill valve having a tendency to interfere with and possibly dislodge any anatomical tissue sample attached to and carried by the distal end of the laprascopic instrument, as it is being removed from the trocar. That is, the use of laprascopic and/or endoscopic surgical techniques to obtain tissue samples of organs or other bodily tissue is universally recognized as a preferred alternative to major invasive surgery for the reasons set forth above. Accordingly, reliability in retrieving any tissue samples that are collected during a procedure is important.

Yet another disadvantage of the duckbill valve involves the loss of elastic memory which sometimes results when the medical instrument is repeatedly inserted in and removed from the trocar while passing through the duckbill valve. Alternatively, elastic memory loss can occur if the medical instrument remains in place on the interior of the trocar and through the duckbill valve for an extended period of time. In either situation, the material from which the converging flap structures are formed may partially lose elastic memory at least to the extent of preventing the distal ends thereof from completely closing into the normally sealed orientation. The failure of the flap structures to completely close may result in an unwanted and inadvertent venting of the insufflation gas upon removal of the instrument from the trocar. In addition, the aforementioned loss of elastic memory and the at least partial separation of the distal ends of the flap structures may cause a continuous or periodic "flapping" of the distal ends and a resulting noise, such as a "humming" sound, which is undesirable during the surgical procedure being undertaken.

In attempting to overcome the above-noted disadvantages associated with the use of the duckbill and other types of valves or seals, attempts have been made to develop devices or structures which are operative to dilate a seal or valve into a position that is out of engagement with the instrument passing through the trocar. More specifically, such devices are intended to facilitate the insertion, and in particular, the removal of medical instruments from the interior of the trocar, which are axially positioned relative to a valve or seal associated with the trocar.

It is to be understood that axial movement of the instrument may be made easier by reducing or eliminating the contact between the seal and the exterior surface of the instrument, as well as the distal tip thereof, as the instrument is being withdrawn from the trocar. However, the structural development and implementation of such a seal opening assembly is made more difficult due to the fact that a wide variety of seals or valves, other than a duckbill valve, are commonly used with the many different types of trocars presently available.

Therefore, there is a long recognized need in the medical field for a seal positioning assembly which is structured to selectively open and close a valve or seal regardless of its structure in order to overcome the recognized disadvantages associated with a duckbill valve or seal. If any such improved seal positioning assembly were developed it should have the structural and functional versatility to be used with a large number of different types of seals or valves, other than the specifically described duckbill valve, thereby rendering it useable with a variety of different types of trocar assemblies or other instrumentation associated with laprascopic or endoscopic surgical procedures. Also, if any such improved seal positioning assembly were developed, it should be structured to be operable in an efficient manner by the physician or medical personnel involved in the surgical procedure, without interfering with the technique normally practiced by the physician during the use of the trocar assembly. Also, the structural and functional features of any such improved assembly should be such as to allow selective positioning of a seal between a seal open orientation and a seal closed orientation in order to accommodate a variety of differently sized medical instruments, while reducing or eliminating the frictional engagement between a valve or seal structure and the instrument, as well as facilitating the removal of anatomical tissue from the body cavity and from the interior of the trocar assembly, as the instrument is withdrawn there from. Finally, if any such improved seal positioning assembly were developed, it would ideally also be capable of overcoming problems associated with duckbill valves or like sealing structures relating to the loss of elastic memory, by generally assuring that the converging flaps or other sealing structures will assume a completely closed and sealed orientation, once a medical instrument has been removed from the trocar assembly and/or sealing valve.

SUMMARY OF THE INVENTION

The present invention is intended to present a solution to these and other needs in the art, and as such, is directed to a seal positioning assembly which may be considered to be a part of an associated seal or valve structure or which may be used in association therewith. Moreover, the seal positioning assembly of present invention is primarily, but not exclusively, structured for use in a trocar assembly, or similar medical instrument, typically used in the performance of laprascopic and/or endoscopic surgery. As such, the seal positioning assembly of the present invention includes a positioning device cooperatively disposed and structured with the associated seal or valve structure such that relative movement there between may serve to selectively open or close the valve or seal structure. As explained in greater detail hereinafter, the various preferred embodiments of the present invention involve relative movement between the positioning device and the seal or valve structure in a rotational, linear, co-axial or other appropriate direction in order to accomplish selective disposition of the valve structure into the open and/or closed orientations.

By way of example, and for purposes of clarity, the seal positioning assembly of the present invention will be described for use with a seal or valve structure of the type generally categorized as having a "duckbill" configuration. However, it is emphasized that the seal positioning assembly of the present invention, with little or no structural modification, may be used with a variety of different seal structures. As such, a primary area of practical application of the present invention is in the medical field for use in selectively opening or closing a seal and/or valve associated with a trocar assembly. As set forth above, such seals are used to significantly reduce or eliminate the escape of insufflation gas from an inflated body cavity during a laprascopic procedure, such as when a laprascopic or like medical instrument is not present in the trocar and/or is not axially disposed within the duckbill valve. Therefore, the various preferred embodiments of the seal positioning assembly of the present invention are described for use with a valve or seal structure capable of being used with a trocar assembly. However, it is within the intended spirit and scope of the present invention to provide a seal positioning assembly structured to regulate the positioning of seals or valves of the type used in a variety of areas, other than medical instrumentation.

Therefore, at least one preferred embodiment of the seal positioning assembly of the present invention is structured to provide for the selective orientation of a seal or valve out of engagement with an instrument passing axially there through. As such, the seal or valve, which would normally engage the outer surface of an axially disposed instrument, is positioned out of contact therewith so as to reduce the frictional engagement between the seal and the exterior surfaces of the instrument. During a laprascopic surgical procedure, it is well known to collect anatomical tissue by securing it to the distal end of the instrument. Therefore, the selective opening of the seal or valve out of engagement with the instrument has the added advantage of preventing any inadvertent detachment or removal of the collected sample of tissue from the end of the instrument.

The versatility of the various embodiments of the seal positioning assembly of the present invention is further demonstrated by the operative features thereof which overcome known disadvantages and problems associated with duckbill valves and other seal structures used with trocar assemblies. More specifically, during or after a laprascopic surgical procedure, the desufflation of an inflated body cavity is required. Typically the venting of the insufflation gas through the trocar is accomplished by opening a stopcock or like venting structure in that the duckbill valve is conventionally disposed and structured to prevent the escape of the insufflation gas when a medical instrument is not positioned therein. However, a typical stopcock structure has a relatively small opening of generally about 1/16 of an inch. As a result, the desufflation of the body cavity by the venting of gas flow through such a small vent opening is time consuming. Therefore, when it is desired to accomplish a more rapid desufflation, the various preferred embodiments of a positioning device of the present invention may be disposed in an open orientation. As a result, the converging flap structures of the duckbill valve are purposefully separated into an open position, thereby facilitating the rapid escape of the insufflation gas through and past the duckbill valve.

Accordingly, one or more preferred embodiments of the seal positioning assembly of the present invention comprise a positioning device including a base and an expander structure connected to the base. The base and the expander structure may be movable with one another on the interior of the trocar assembly with which the seal positioning assembly is used. Moreover, in at least one embodiment, the expander structure is dimensioned and configured to at least partially correspond to the interior configuration of the seal or valve with which it is associated, at least for the purpose of facilitating a mounting or positioning of the expander structure on the interior of the seal. Further, the positioning device, including the expander structure, is capable of being moved relative to the seal or valve and thereby selectively assume either a seal open orientation or a seal closed orientation. As will be explained in greater detail hereinafter, movement of the positioning device relative to the seal or valve may be in a rotational, axial or other appropriate direction, dependent at least in part on the structure, configuration, and disposition of the positioning device, seal or valve, trocar assembly and/or other instrumentation with which the seal positioning assembly is used. Accordingly, when the positioning device is movable in a rotational direction, the axis of rotation of the expander structure is preferably coincident to the longitudinal axis of a passage or channel extending through the seal. In at least one embodiment the a channel is provided in the positioning device which also defines the path along which the penetrating or like instrument travels through the trocar as it enters or is withdrawn from the body cavity defining the surgical site.

Therefore, at least one preferred embodiment of the positioning device of the present invention comprises the expander structure at least partially defined by a plurality of expander members. One or more preferred embodiments of the present invention are described and represented as including two such expander members. However, additional preferred embodiments may include more than two expander members such as, but not limited to, four expander members. When two expander members are utilized they are disposed in substantially opposed, spaced relation to one another and extend outwardly from the base so as to be readily disposable into the interior of the seal or valve. Each of the expander members may be correspondingly dimensioned and configured, wherein the overall structure thereof may be at least partially dependent upon the interior surface configuration of the seal or valve with which the expander structure is used. Therefore, one preferred embodiment of the present invention comprises each of the expander members having a proximal end secured to the base and extending outwardly there from into a terminally disposed distal end. Further, each of the expander members comprises a converging configuration extending along the length thereof from the proximal end towards the distal end. As such, this preferred embodiment of the present invention is readily adapted for use with a variety of different seals or valves but is particularly adaptable for use with a duckbill valve or seal well known and used in the medical field.

Yet another preferred embodiment of the seal positioning assembly of the present invention includes the expander structure comprising two spaced apart expander members each comprising a somewhat elongated, finger-like configuration having a proximal end secured to the base and a distal end disposed outwardly there from into the interior of the seal with which the expander structure is associated.

In either of the above noted preferred embodiments, the seal positioning assembly of the present invention further comprises the above mentioned channel extending through the base and between the expander members of the positioning device. The channel is disposed in substantially coaxial alignment with the associated duckbill valve. As such, an instrument passing through the valve or seal, also passes through the channel of the positioning device. Whether or not the medical instrument is positioned within the seal, the various preferred embodiments of the positioning device are disposed and structured such that relative movement between the expander structure and the seal or valve serves to selectively open or close the seal or valve. As will be described in greater detail hereinafter, relative movement between the positioning device and expander structure may be defined by movement of the positioning device relative to the seal or valve or alternatively, movement of the seal or valve relative to the positioning device. It is also to be noted that the positioning device may be disposed, moved and/or oriented interiorly or exteriorly of the seal or valve, dependent on the specific structural features of the preferred embodiment of the seal positioning assembly being utilized.

Again, with the various preferred embodiments of the present invention, as generally described above, the seal open orientation of the positioning device may be generally defined by relative movement between the expander structure and the seal or valve, such as by rotating or axially disposing the positioning device, until the expander members are disposed in engaging relation with predetermined interior surface portions of the seal or valve. When in such an engaging position, the predetermined surface portions of the seal are forced outwardly, away from one another causing the seal or valve interior to expand and open. The seal or valve is thereby disposed out of contact with the exterior of the axially disposed instrument. The instrument is thereby allowed to pass through the seal or valve without frictional engagement therewith and without fear of an anatomical issue being inadvertently dislodged there from. Rapid venting of the insufflation gas may also be accomplished in this manner, as set forth above. Disposition of the seal or valve in the aforementioned closed orientation may be accomplished by rotation or other appropriate movement of the expander structure within and/or relative to the seal or valve, until the expander members are removed from or disposed in substantially aligned relation with the predetermined interior surfaces of the seal or valve.

Yet another preferred embodiment of the seal positioning assembly of the present invention is provided to overcome problems and disadvantages associated with seal or valve structures, particularly duckbill valves, relating to a loss of elastic memory. More specifically, after repeated or prolonged use, the converging flap structures of the duckbill valve may have a tendency to remain at least partially open and in an unsealed orientation when a laparoscopic or other medical instrument is not positioned within the valve or seal structure. As a result, inadvertent venting of the insufflation gas may occur through the duckbill valve. Also, the loss of elastic memory may result in a periodic or substantially continuous "flapping" of the distal ends of the converging flaps and the generation of an undesirable "humming" or like noise. Therefore, the seal positioning assembly of the present invention comprises a biasing assembly mounted on the exterior of a duckbill valve. The biasing assembly comprises a plurality of biasing members each secured to and extending laterally outward from the exterior surface of a different one of the converging flap structures of the duckbill valve. Further, the biasing structures are disposed, dimensioned and configured to engage correspondingly disposed interior surfaces of a trocar housing in which duckbill valve or like seal structure is mounted. In addition, each of the protruding biasing members are formed from a material having sufficient elasticity and/or flexibility to allow separation of the converging flaps and intentional opening of the duckbill valve structure when a laparoscopic or other medical instrument passes there through. Similarly, the valve or seal structure can be easily opened by movement of the aforementioned positioning device relative to the valve or seal, such as when the expander structure is intentionally positioned into the aforementioned open orientation, causing a separation of the flap structure against the closing force normally provided by the biasing assembly.

As will be noted from the above description, numerous preferred embodiments of the present invention include an expander structure, movable in an appropriate direction relative to a seal or valve structure of the type primarily, but not exclusively, adapted for use with a trocar assembly. Moreover, a common structural and operative feature of certain ones of the preferred embodiments of the present invention comprise the expander structure disposed within and/or movable interiorly of the seal or valve structure as it is disposed in either the seal open orientation or the seal closed orientation. However, the structural and functional versatility of the seal positioning assembly of the present invention is further demonstrated in additional preferred embodiments, wherein a seal or valve structure is selectively opened or closed by relative movement between the positioning device and/or expander structure and the seal or valve structure. Such relative movement may be accomplished by linear, rotational or other appropriate directional movement of the positioning device and expander structure relative to the seal or valve structure. Alternatively, appropriate directional movement or positioning of the seal structure relative to the expander structure of the positioning device may also define the above noted relative movement.

It is also emphasized that additional preferred embodiments of the seal positioning assembly of the present invention are structured such that the positioning device and associated expander structure are disposed on and movable relative to the exterior of the valve structure rather than the interior thereof. Common structural and operative features of the various preferred embodiments of the present invention include the expander structure, which may comprise one or more expander members disposed in forced engagement with predetermined portions of the seal structure. Cooperative disposition and structuring between the positioning device and the seal structure will thereby serve to separate the flaps of the duckbill valve into an open position. As with the previously described preferred embodiments of the present invention, once the valve structure is opened, engagement or contact of the flaps with an instrument passing therethrough is eliminated or significantly reduced. Also, when the positioning device forces the valve structure into an open position, rapid venting of the insufflation gas from a body cavity, through the trocar assembly may be efficiently accomplished.

It is again emphasized that while the various preferred embodiments of the present invention comprise a positioning device including an expander structure which is particularly adaptable for use with a duckbill valve or seal, the structural and functional versatility of the various embodiments is such as to be used with valves or seals having a variety of different structures other than a duckbill configuration. Further, the seal positioning assembly of the present invention is not limited for use with medical instrumentation.

These and other objects, features and advantages of the present invention will become clearer when the drawings as well as the detailed description are taken into consideration.

BRIEF DESCRIPTION OF THE DRAWINGS

For a fuller understanding of the nature of the present invention, reference should be had to the following detailed description taken in connection with the accompanying drawings in which:

FIG. 9B is a perspective view in exploded form of the embodiment of FIG. 9A wherein the positioning device of the seal positioning assembly of the present invention is in a different, operative orientation.

FIG. 14A is cross sectional view in partial cutaway of yet another preferred embodiment of the seal positioning assembly of the present invention, as taken along line 14A-14A of FIG. 14B.

FIG. 14B is a cross sectional view along line 14B-14B of the embodiment of FIG. 14A.

FIG. 15A is a cross sectional view in partial cutaway of yet of the embodiment of FIGS. 14A and 14B but in a different operative position and taken along line 15A-15A of FIG. 15B.

FIG. 15B is a sectional view taken along line 15B-15B of the embodiment of FIG. 15A.

FIG. 17A is a cross sectional view in partial cutaway of the embodiment of FIGS. 16A and 16B but in a different operative position and taken along line 17A-17A of FIG. 17B.

FIG. 17B is a sectional view of the embodiment of FIG. 17A taken along line 17B-17B.

FIG. 18A is a sectional view in partial cutaway of yet another preferred embodiment of the seal positioning assembly of the present invention, as taken along line 18A-18A of FIG. 18B.

FIG. 18B is a sectional view of the embodiment of FIG. 18A taken along line 18B-18B.

FIG. 19A is a sectional view in partial cutaway of the embodiment of FIGS. 18A and 18B but in a different operative position and taken along line 19A-19A of FIG. 19B.

FIG. 19B is a sectional view of the embodiment of FIG. 19A taken along line 19B-19B of that Figure.

Like reference numerals refer to like parts throughout the several views of the drawings.

DETAILED DESCRIPTION OF THE INVENTION IN PREFERRED EMBODIMENT(S)

Figure 1:
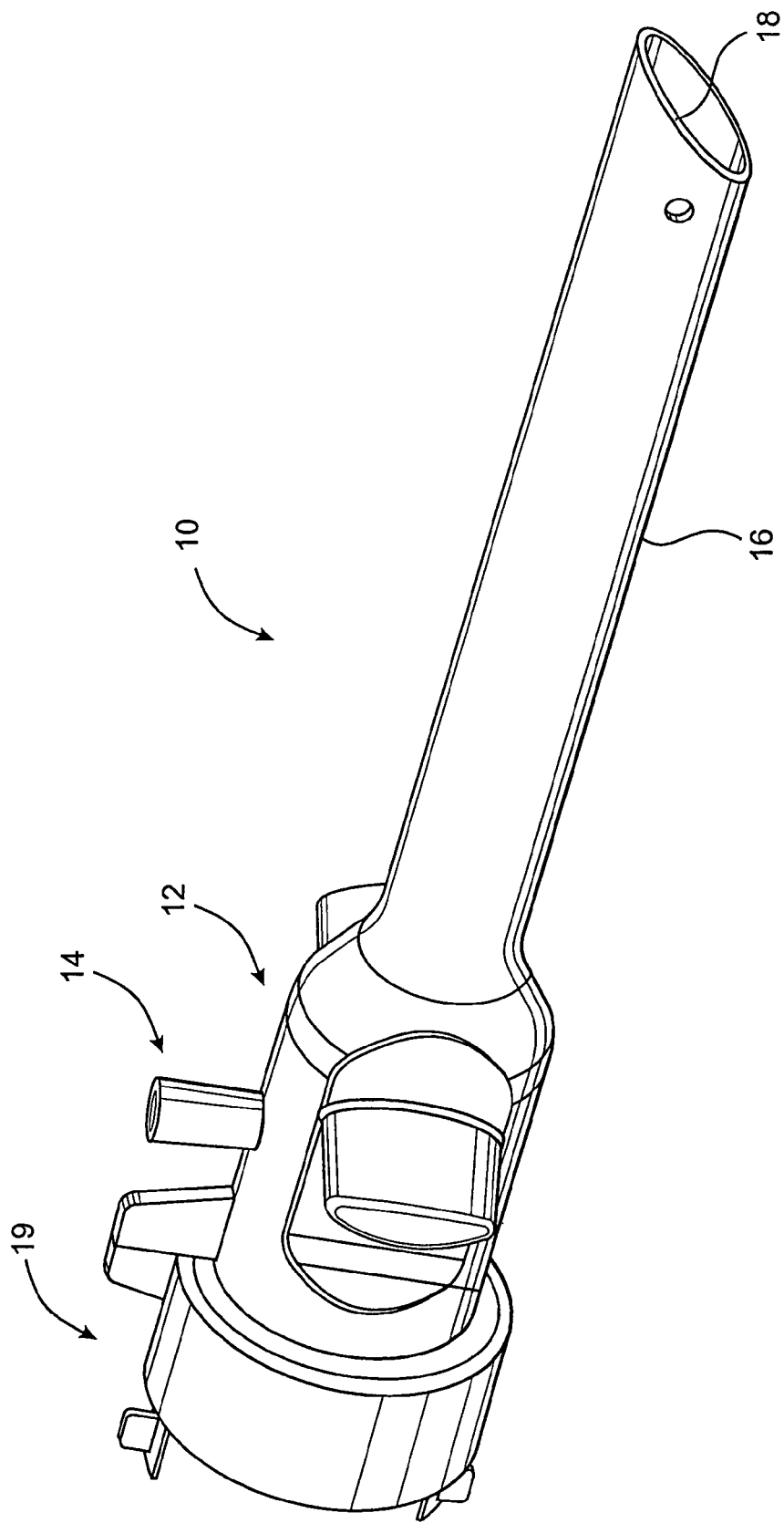
FIG. 1 is a perspective view of a trocar assembly intended to be representative of a variety of different trocar structures with which the seal positioning assembly of the present invention may be utilized.
Figure 2:
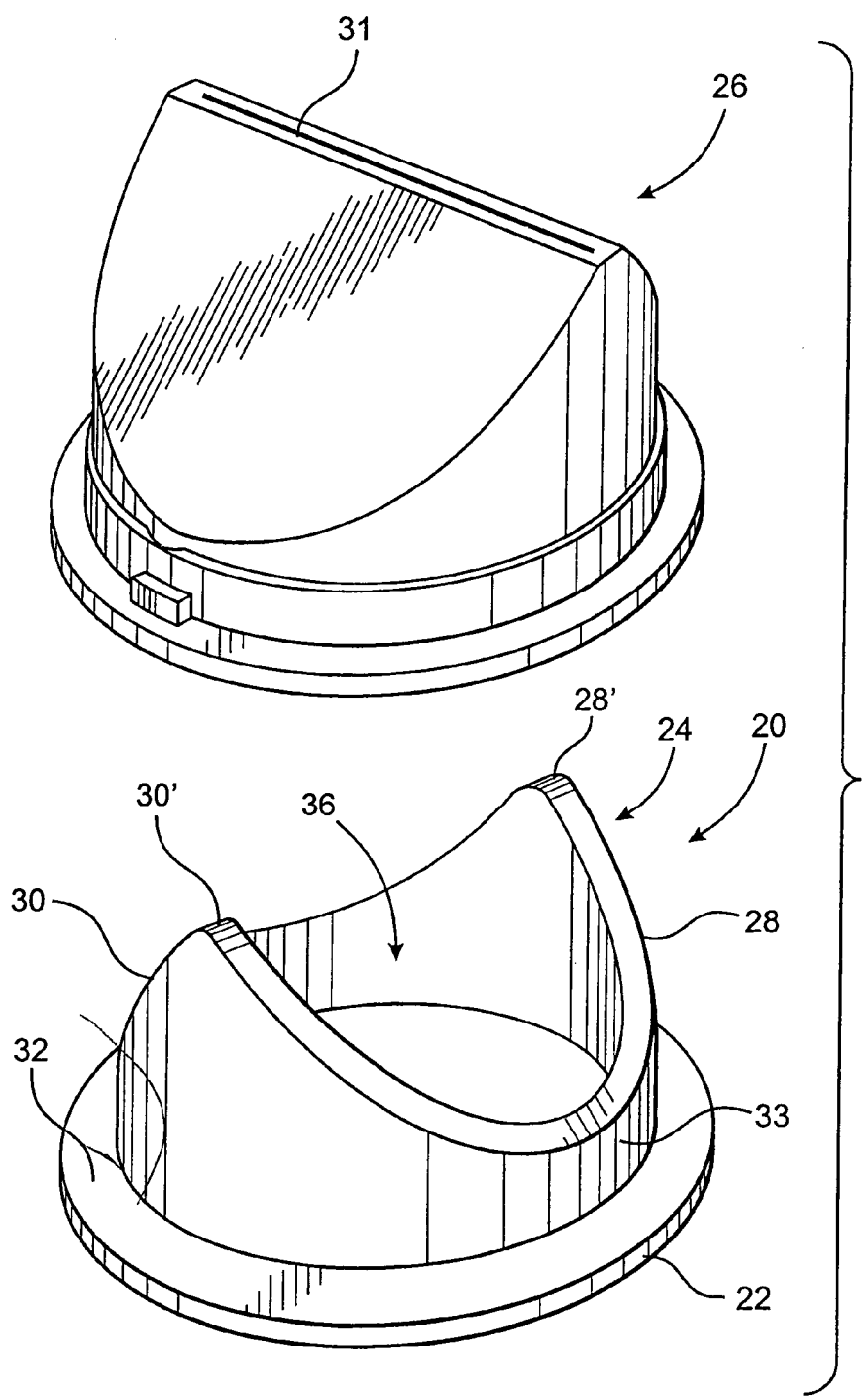
FIG. 2 is a perspective view in exploded form of the seal positioning assembly of the present invention and one of a plurality of seal members with which it may be used.
Figure 3:
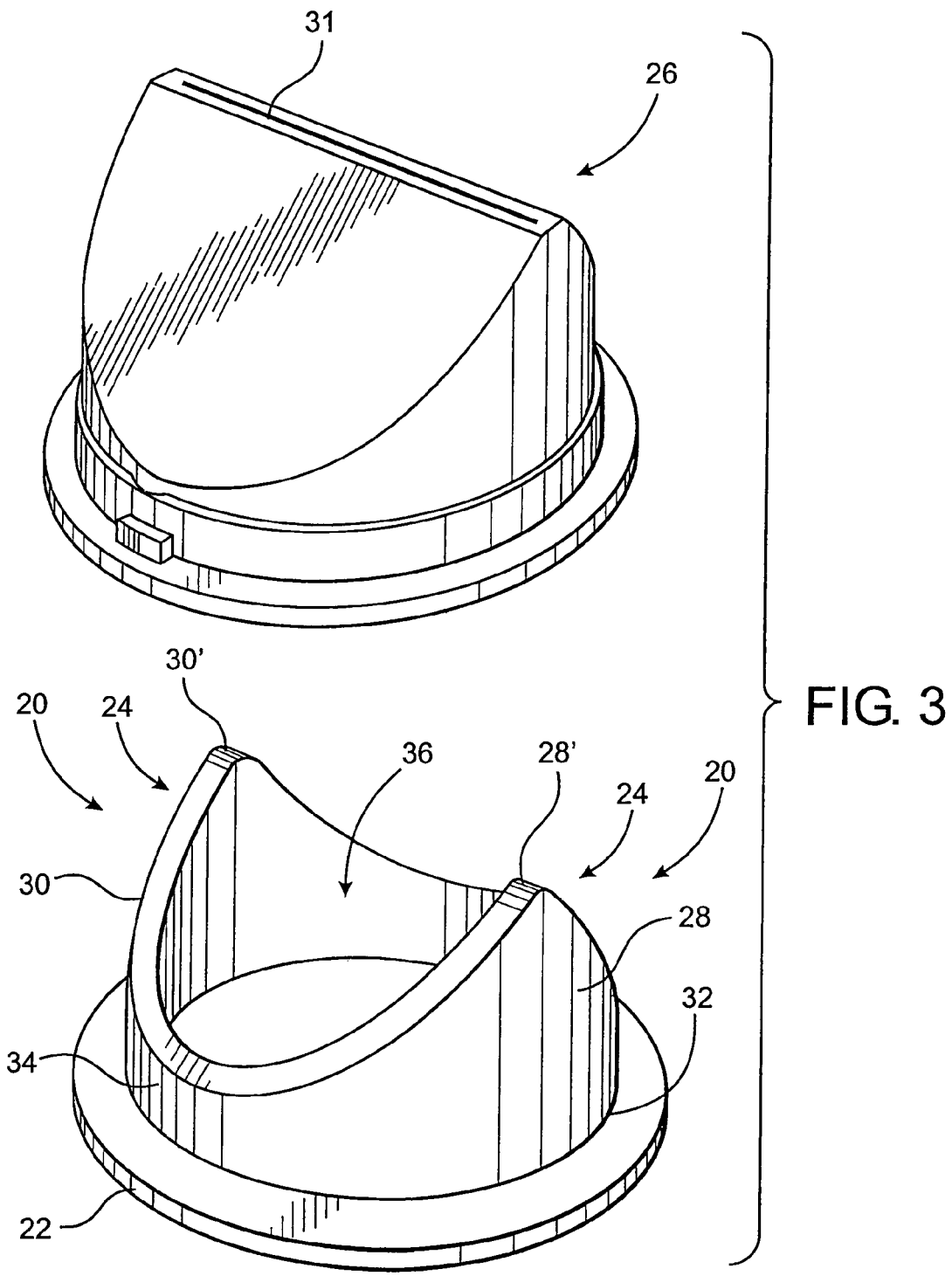
FIG. 3 is a perspective view in exploded form of the seal positioning assembly of the embodiment of FIG. 2 in a different orientation.

As shown in the accompanying Figures, the present invention is directed towards a seal positioning assembly which may be considered as part of a seal assembly or which may be used in conjunction therewith, but otherwise considered independent thereof. As described in greater detail hereinafter, the seal positioning assembly may be used with medical instruments of the type used for minimally invasive surgery such as laprascopic and/or endoscopic surgery. Therefore, for purposes of clarity, the seal positioning assembly of the present invention is described for use in the medical field such as by being mounted within a trocar assembly generally indicated as 10 in FIG. 1. Also, as should be apparent, the terms "seal structure" and "valve structure" as well as "seal" and "valve" are used interchangeably herein when referring to the duckbill valve 26 or like structures associated with the various preferred embodiments of the present invention.

Whether considered a part of a seal or valve structure or used independently thereof, but in direct association therewith, the seal or valve structure as well as the seal positioning assembly are mounted within the trocar assembly. Moreover, the seal positioning assembly is operable to dispose the seal or valve into an open orientation or a closed orientation. As will be explained in greater detail hereinafter, when the seal positioning assembly and seal or valve are in an open orientation, the seal or valve is maintained substantially out of contact or engagement with an instrument passing axially through the seal positioning assembly and the associated seal or valve. Also, the seal open orientation of the seal or valve and seal positioning assembly according to the present invention facilitates rapid desufflation or venting of the insufflation gas from a patient's body cavity through the trocar assembly. It is pointed out, however, that the trocar assembly 10 disclosed in FIG. 1 includes a distinctive shape and structure that has been developed by and which is proprietary to Taut, Inc. of 2571 Kaneville Road, Geneva, Ill. 60134. However, the trocar assembly 10 illustrated is intended to be representative of any of a variety of different trocar assemblies with which the seal positioning assembly of the present invention may be utilized.

Accordingly, the trocar assembly 10 or another equivalently functioning trocar assembly, typically includes a trocar housing 12 which may have a connector port structure 14 communicating with the interior of the housing 12. The connector structure 14 serves to establish interconnection with a supply of fluid, such as carbon dioxide gas, used to inflate a body cavity during laprascopic or endoscopic surgery. The trocar assembly 10 also includes an elongated cannula or trocar sleeve 16 dimensioned and structured to removably receive an obturator (not shown) or other instrument disposed to pass axially through the trocar assembly 10 along the cannula 16 and through one or more valves typically mounted within the housing 12. The one or more valves, which will be explained in greater detail hereinafter, are provided to prevent or significantly reduce the escape of the insufflation gas, once the body cavity has been inflated. Other structural features of the trocar assembly 10 include the provision of an open end 18 of the trocar sleeve, through which an axially disposed instrument passes as it enters a body cavity. Also, the trocar 10 may include a mounting hub 19 secured to a proximal end thereof in communication with the housing 12. The mounting hub 19 is provided to facilitate the connection of an obturator or other instrument to the trocar, as is well known in the medical field.

With primary reference to FIGS. 2 through 5, at least one preferred embodiment of the seal positioning assembly of the present invention comprises a positioning device generally indicated as 20 including a base 22 and an expander structure, generally indicated as 24. Both the base 22 and the expander structure 24 may assume a variety of different structural configurations so as to facilitate the opening and closing of a seal, generally indicated as 26, with which it is operatively associated. Further, at least some of the preferred embodiments of the expander structure 24 are dimensioned and configured to be mounted within the interior of the seal 26, as demonstrated in FIGS. 4 and 5. As will also be explained in greater detail hereinafter, in at least some of the preferred embodiments of the present invention, the positioning device 20 is movable in a rotational, axial or other appropriate direction relative to the valve structure 26 and into an open orientation or a closed orientation so as to open or close the valve structure 26.

Accordingly, the expander structure 24 is preferably, but not necessarily, rotationally mounted within the interior of the valve 26 and the base 22 is disposed at least partially on an exterior thereof. In the embodiment of FIGS. 2 through 8 the base 22 may be disposed to manipulate the seal positioning device 20 so as to facilitate rotation, or other appropriate movement, of the expander structure 24 between a seal closed orientation, as demonstrated in FIG. 4, and a seal open orientation as demonstrated in FIG. 5. In order to accomplish the movement of the expander structure 24 relative to the seal 26, additional structure may be associated with or be defined as part of the base 22, or other portions of positioning device 20 so as to facilitate appropriate movement of the expander structure 24 within the interior of the seal 26 and, between the seal closed and seal open orientations.

The expander structure 24 of the embodiment of FIGS. 2 through 5 comprises two spaced apart expander members 28 and 30 having a proximal end, as at 32, integrally or otherwise fixedly secured to one face of the base 22. Each of the expander members 28 and 30 extend outwardly from the base 22 in a substantially common direction and terminate at spaced apart distal ends 28' and 30'. As such, each of the expander members 28 and 30 comprise a substantially converging configuration along their length as they extend outwardly from the proximal end 32 to the respective distal ends 28' and 30'. In addition, the expander members 28 and 30 may be disposed in spaced, separated and opposing relation to one another. Alternatively, as shown in the preferred embodiment of FIGS. 2 and 3 the expander structure 24 includes interconnecting sidewalls 32 and 34 which extend outwardly from a common face of the base 22 a lesser distance than that of the expander members 28 and 30.

Other structural features of the seal positioning device 20 include the provision of a channel 36 extending through both the base 22 and the expander structure 24. Moreover, the expander members 28 and 30 as well as the interconnecting sidewalls 32 and 34 substantially surround the channel 36 and at least partially define the boundaries thereof. As represented, the channel 36 is centrally disposed along a central longitudinal axis of the seal positioning device 20 in communicating relation with the interior of the valve member 26 and in alignment with a central longitudinal axis of the seal member 26. The channel 36 also defines a path of travel of an instrument passing axially through the valve or seal 26 as it slides through the interior of the trocar assembly 10, as the instrument is being positioned within or withdrawn from a body cavity of a patient which defines the surgical site.

Figure 4:
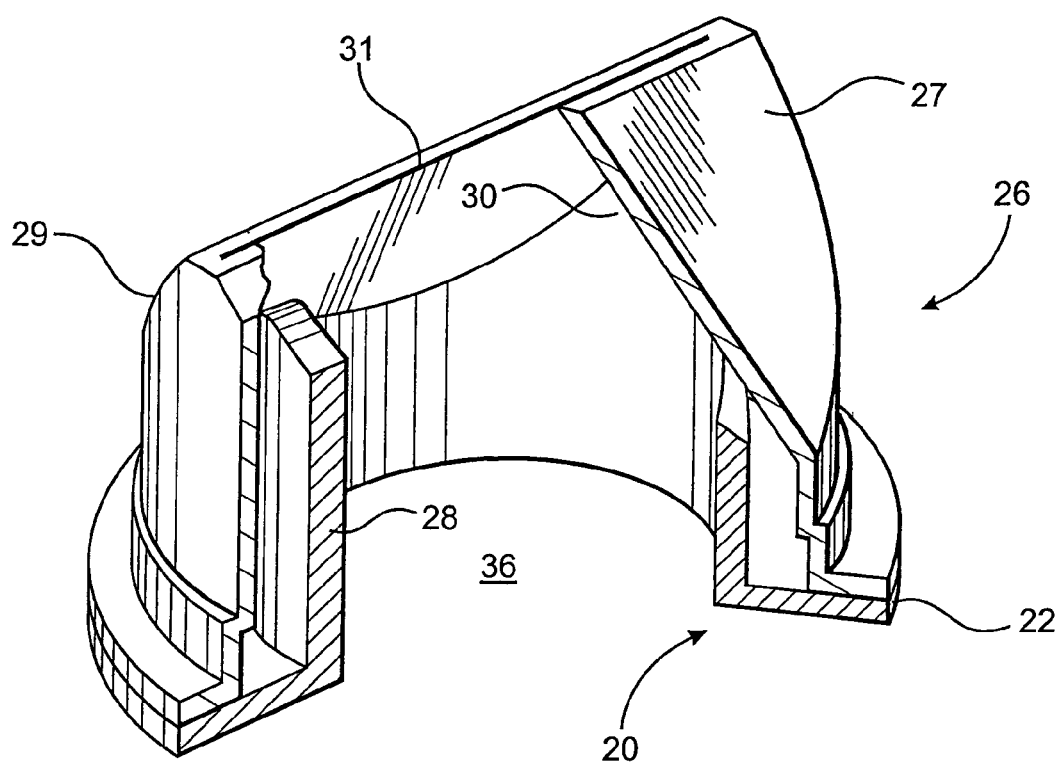
FIG. 4 is a perspective view in partial cutaway showing interior portions of the seal member and seal positioning assembly of the embodiment of FIGS. 2 and 3 in a seal closed orientation.
Figure 5:
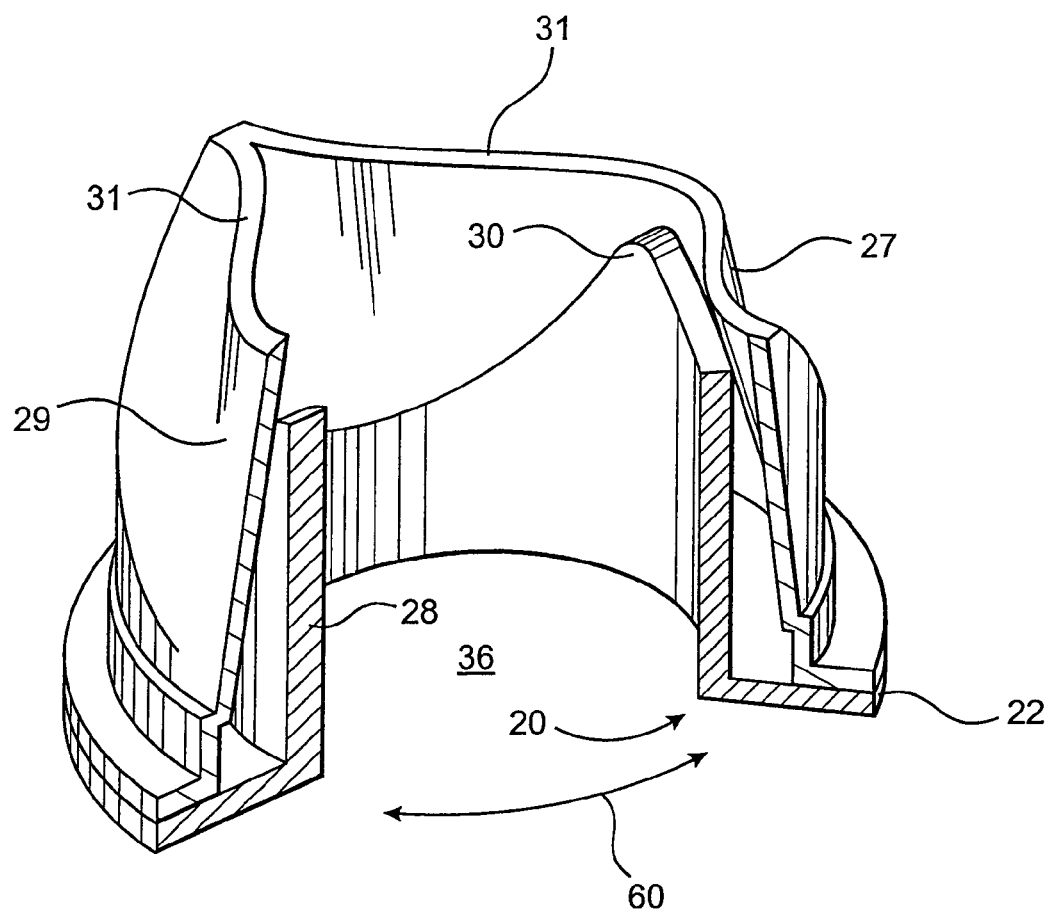
FIG. 5 is a perspective view in partial cutaway showing interior portions of the seal member and the seal positioning assembly of the embodiment of FIGS. 2 through 4 in a seal open orientation.

From a review of the accompanying FIGS. 2 through 8, it is apparent that the seal or valve member 26 is in the form of a "duckbill" seal or valve comprising two substantially opposing, converging flaps 27 and 29 terminating in outer ends which collectively define a valve opening 31. Due to the elastic memory and inherent bias of the material and overall structure of the converging flaps 27 and 29, the valve opening 31 is normally disposed in a closed orientation as represented in FIG. 4. Therefore, the axial positioning of an instrument on the interior of the trocar assembly 10, through the valve opening 31 will not establish a sealing engagement between the distal ends of the flap structures 27 and 29. However, the flap structures 27 and 29 will engage or contact the exterior surface of the instrument, which frequently results in frictional forces being exerted on the flap structures 27 and 29. Such forces have been known to cause an inversion of the flaps 27 and 29, as well as an inadvertent displacement of anatomical tissue secured to the distal end of the instrument as it is being withdrawn from the body cavity through the interior of the trocar assembly 10. In order to avoid such problems, one important feature of the positioning device 20 of the present invention is its selective movement such as, but not limited to, a rotation thereof on the interior of the valve member 26 between the valve closed orientation of FIG. 4 and the valve open orientation of FIG. 5.

Accordingly, the expander structure 24 is preferably disposed in the valve closed orientation of FIG. 4, prior to entrance of the instrument into the interior of the trocar assembly 10. Escape of insufflation gas from the body cavity is thereby prevented or significantly reduced when the medical instrument is absent from the trocar. However, when it is desired to withdraw the instrument from the interior of the body cavity, back through the seal member 26, or accomplish a rapid venting of the insufflation gas from the body cavity in the absence of the medical instrument, the physician or other medical personnel manipulates the positioning device 20, such as by rotating accessible portions thereof until the expander structure 24 is disposed in the valve open orientation of FIG. 5.

The valve open orientation of this preferred embodiment is thereby at least partially defined by a forced engagement of the expander structure 24 and more specifically the expander members 28 and 30, with opposed, interior surface portions of the converging flaps 27 and 29. More specifically, the expander structure 24 is rotated, as schematically represented by directional arrow 60, within the seal member 26 at least until the expander members 28 forcibly engage the interior surface portions of the valve structure 26 and exert an outwardly directed force on the converging flaps 27 and 29 to the extent that the valve opening 31 is opened. The size of the opening 31 may be varied by the degree of rotation applied to the expander structure 24, such as by being rotated through an arc of up to approximately 90 degrees. Of course, the degree of rotation of the expander structure 24 may be less or more than 90 degrees, but should be sufficient to separate the flaps 27 and 29 and open the seal opening 31 an adequate distance to facilitate passage of the instrument through the seal member 26 without contact or sealing engagement there between.

With primary reference to FIG. 4, the expander structure 24, including the expander members 28 and 30, is thereby rotated into or out of the seal closed orientation again by manipulation of an accessible portion of the base 22 or other portion of the positioning device 20. As such, the seal closed orientation may be at least partially defined by the expander members 28 and 30 disposed in spaced relation to the opposed interior surface portions of the converging flaps 27 and 29. The seal closed orientation may also be defined by a substantial alignment of the two expander members 28 and 30 relative to the elongated seal opening 31 as disclosed.

Figure 6:
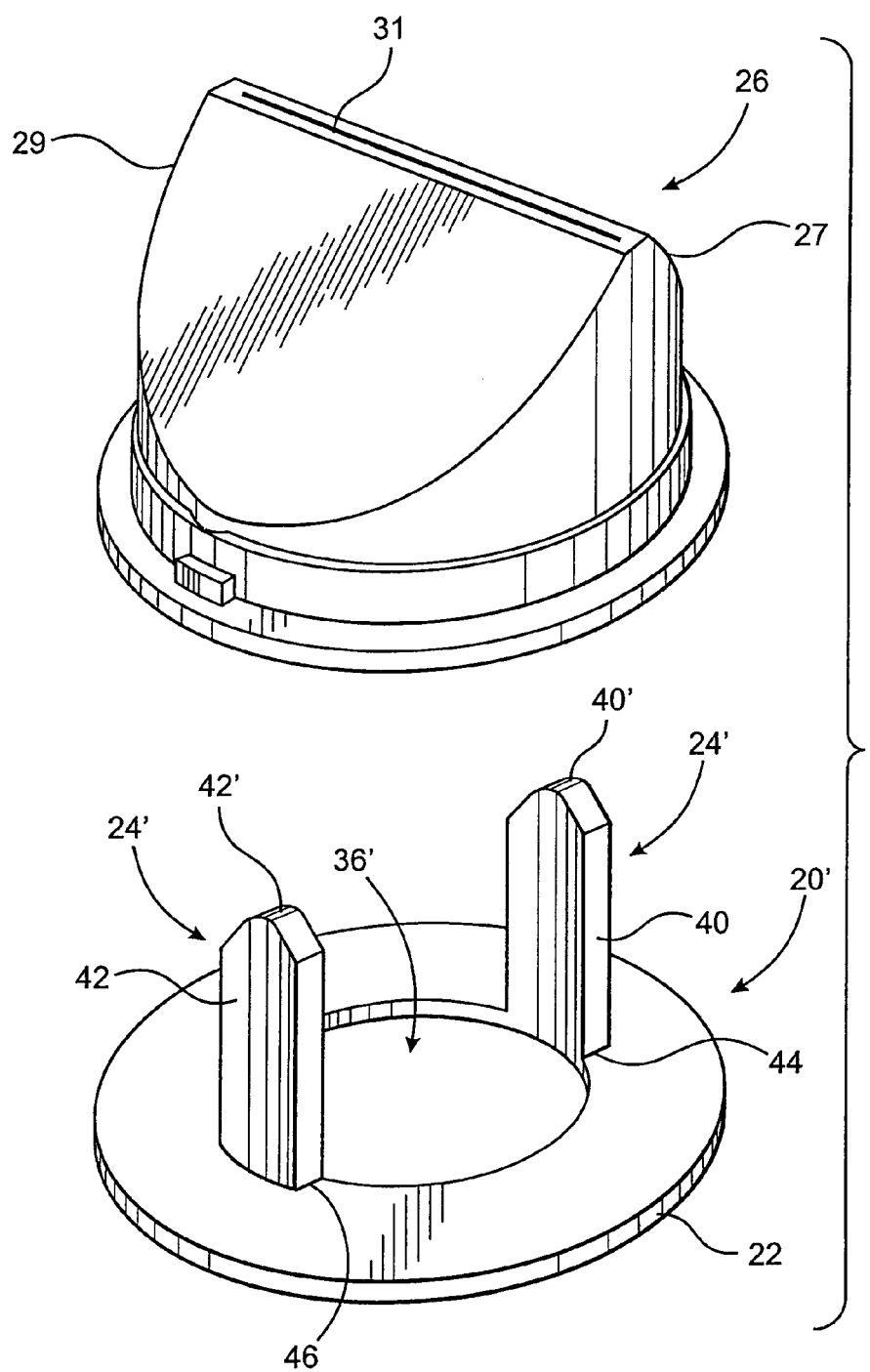
FIG. 6 is a perspective view in exploded form of yet another preferred embodiment of the seal positioning assembly of the present invention and the seal structure associated therewith.
Figure 7:
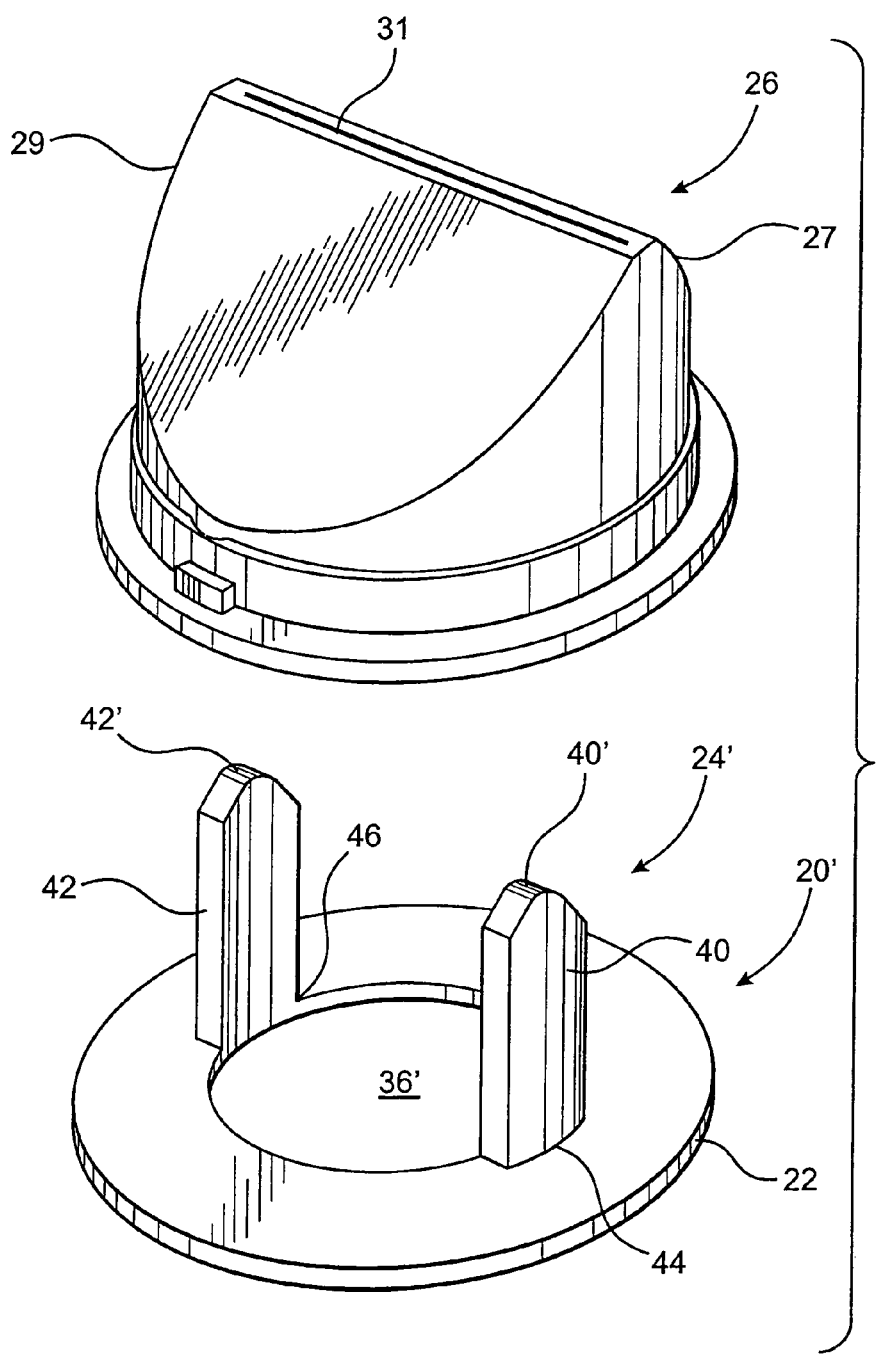
FIG. 7 is a perspective view in exploded form of the embodiment of FIG. 6 in a different orientation.

Yet another preferred embodiment of the present invention is represented in FIGS. 6 and 7. More specifically, the positioning device 20' of this embodiment comprises the base 22 having a channel 36' extending there through. In addition, the expander structure 24' comprises two spaced apart, substantially opposing expander members 40 and 42. Each of the expander members 40 and 42 include proximal ends 44 and 46 integrally or other wise fixedly secured to the base 22. Moreover, the expander members 40 and 42 each comprise a substantially equally dimensioned, elongated finger-like configuration terminating in respective distal ends 40' and 42'. Further, the expander members 40 and 42 are preferably disposed in parallel relation to one another and also in parallel relation to a central longitudinal axis of the channel 36' extending there between. As with the embodiment of FIGS. 2 through 5, the channel 36' is disposed in aligned relation with the seal opening 31 of the seal structure 26. Also similar to the embodiments of FIGS. 2 through 5, the valve structure 26 is preferably in the form of a duckbill configuration including two converging flaps 27 and 29.

Figure 8:
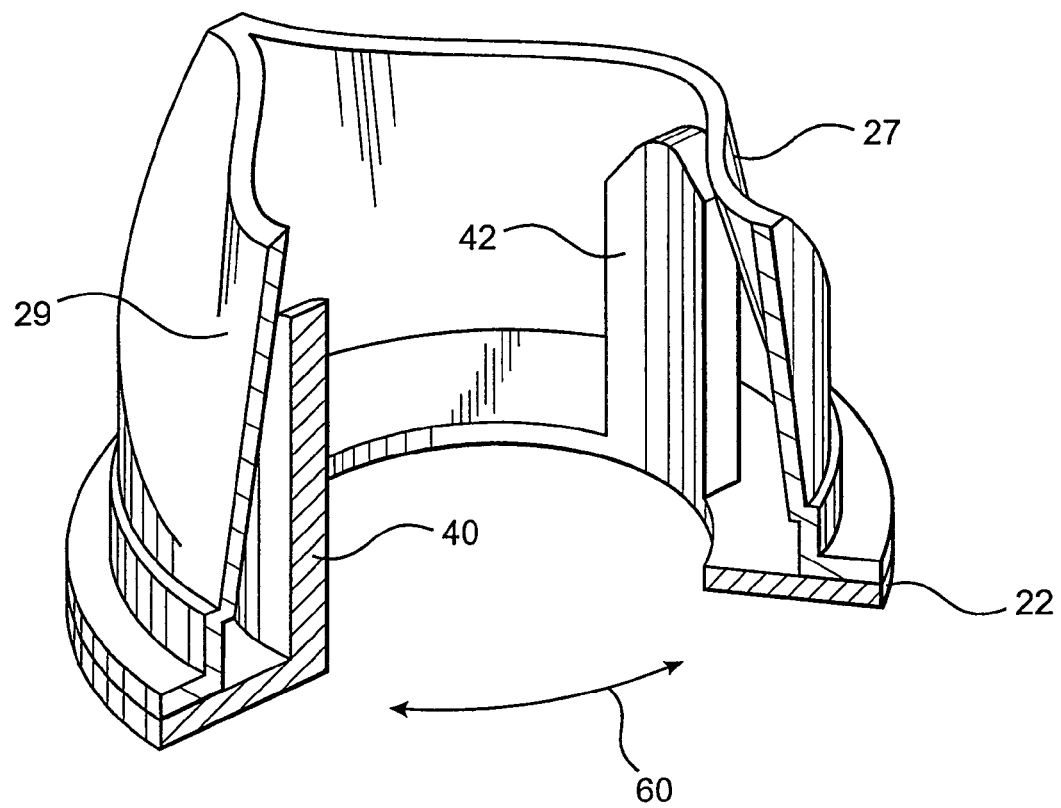
FIG. 8 is a perspective interior view in partial cutaway of the embodiment of FIGS. 6 and 7 in a seal open orientation.
Figure 9A:
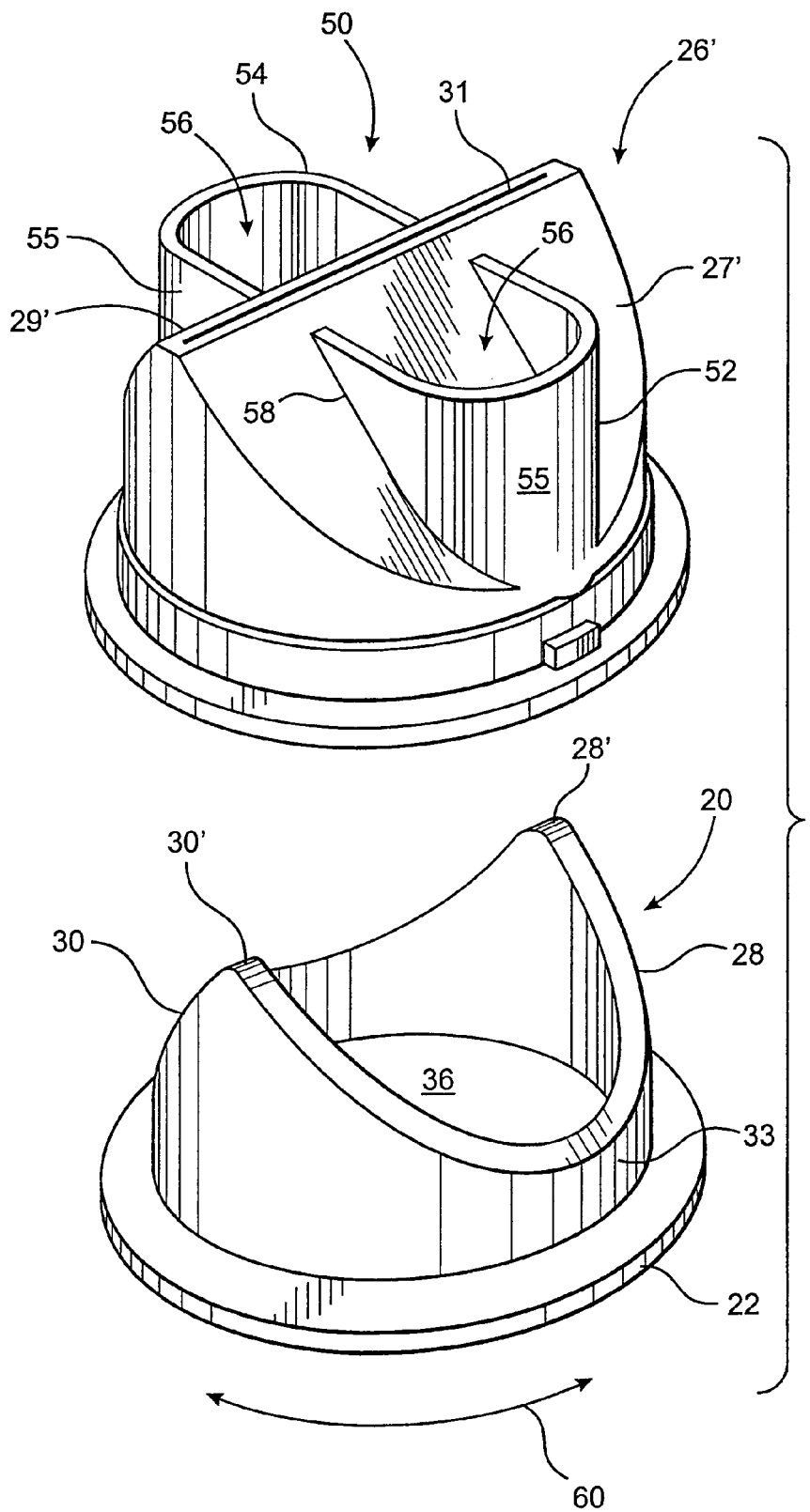
FIG. 9A is a perspective view in exploded form of yet another preferred embodiment relating to a biasing assembly of the seal positioning assembly of the present invention.
Figure 11:
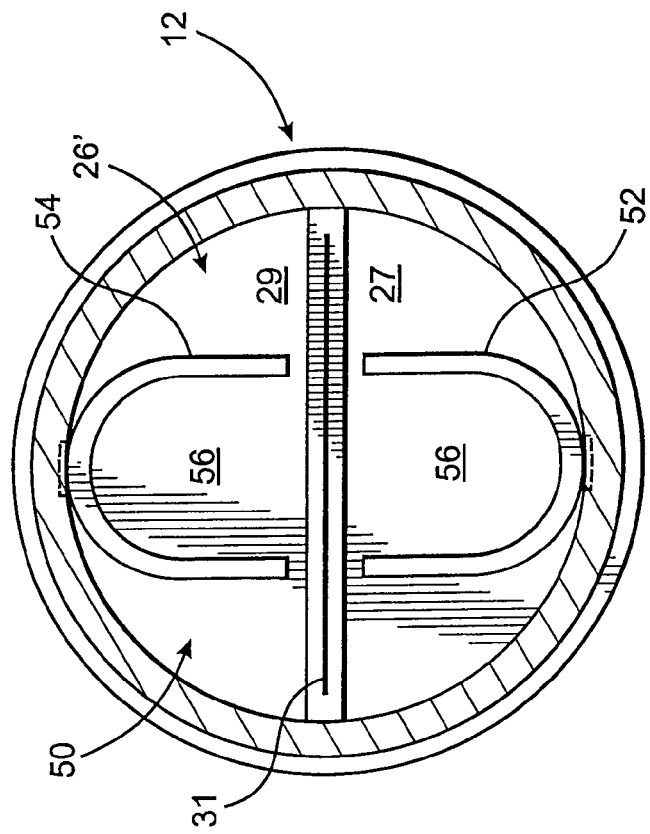
FIG. 11 is an end view in section of the embodiment of FIG. 10.
Figure 10:
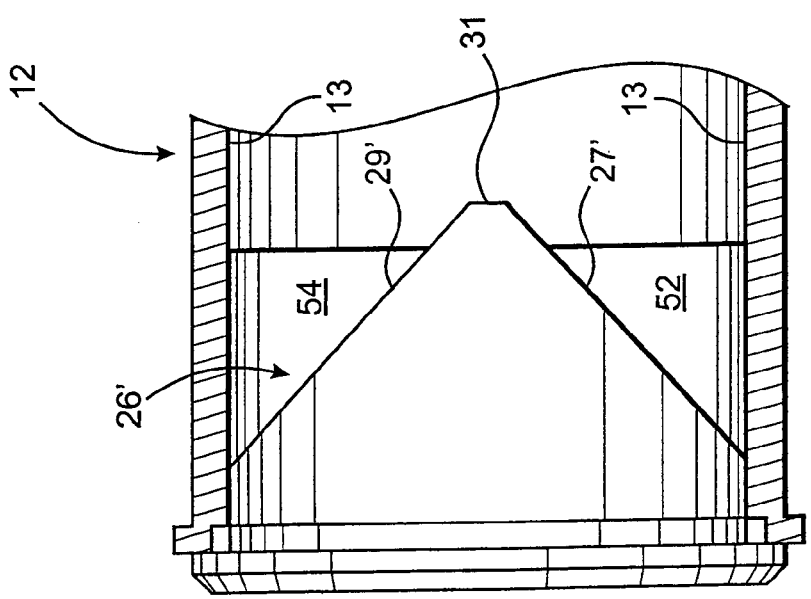
FIG. 10 is a sectional view in partial cutaway of the duckbill valve of the embodiment of FIGS. 9A and 9B shown in an operative, mounted orientation within a trocar assembly.

The expander structure 24' and in particular, the two expander members 40 and 42, are at least partially dimensioned and configured to correspond to the interior of the valve or seal 26. As such, the expander structure 24' is mounted within the interior of the valve or seal 26 and is rotational therein between the seal closed orientation represented in exploded form in FIG. 7 and the seal open orientation of FIG. 8. Rotation of the expander members 40 and 42 between the seal closed orientation of FIGS. 7 and the seal open orientation of FIG. 8 is accomplished by manipulation of an accessible portion of the base 22 or any other appropriate portion of the positioning device 20'. Further, as with the embodiment of FIGS. 2 through 5, the seal closed orientation is defined by the expander members 40 and 42 being disposed in spaced apart relation to opposed interior surface portions of the converging flaps 27 and 29. To the contrary, the seal open orientation is at least partially defined by rotation (or other directional movement) of the expander structure 24' until the expander members 40 and 42 are in a forced engagement with predetermined interior surface portions of the normally converging flaps 27 and 29. Such orientation of the expander members 40 and 42 results in their outwardly forcing engagement with corresponding ones of the flaps 27 and 29 as demonstrated in FIG. 8. Rotation of the seal positioning device 20', as schematically demonstrated by directional arrow 60, relative to the seal 26 may be through an arc of generally about 90 degrees so as to vary the size of the seal opening 31. The size of the instrument passing there through will thereby be accommodated and/or a rapid venting of the insufflation gas from the body cavity through the trocar assembly 10 can be accomplished.

Yet another preferred embodiment of the seal positioning assembly of the present invention is represented in FIGS. 9-13 and comprises a biasing assembly generally indicted as 50. the biasing assembly 50 includes at least one but preferably a plurality of biasing members 52 and 54 mounted on predetermined exterior surfaces of the seal or valve structure 26'. Accordingly, in contrast to the structuring of the positioning device 20 and 20' relative to the valve structure 26, the biasing assembly 50 is connected directly to the valve structure 26' and is thereby specifically associated therewith.

As clearly represented, the valve structure 26' is represented as a duckbill valve, having two converging flap structures 27' and 29' normally disposed or biased into a closed position such that the opening 31 is normally biased into a closed and sealed orientation. However, as set forth above some valve structures, particularly, but not exclusively, a duckbill valve 26' frequently demonstrates a degree of elastic memory loss. As such, repeated or prolonged use of the duckbill valve 26' with a laparoscopic or other medical instrument passing there through frequently results in an incomplete closure or sealing of the opening 31. As a result, the opening 31, when not completely closed or sealed, may allow for inadvertent and unintended venting of the insufflation gas from the body cavity as it flows back through the trocar as well as a periodic or continuous "flapping" of the flap structures.

Therefore, the biasing assembly 50 including the outwardly protruding biasing members 52 and 54 are disposed and structured to at least partially bias and thereby maintain the flap structures 27' and 29' in a closed position such that the opening 31 remains sealed when there is no instrument positioned within the valve structure 26'. With primary reference to FIGS. 10 and 11 the disposition, dimension, and configuration of each of the protruding biasing members 52 and 54 are such as to cooperate with the correspondingly disposed interior surfaces 13 of the trocar housing 12. When the valve structure 26' is operatively positioned on the interior of the trocar housing 12, the biasing members 52 and 54 are disposed into confronting engagement and/or immediately contiguous or adjacent relation to the interior surfaces 13. As such, the corresponding flaps 27' and 29' will be normally biased toward one another so as to seal the opening 31 as clearly indicated.

As represented, the specific structural features of the biasing members 52 and 54 include and outwardly projecting sidewall 55 having a curved configuration at its outermost end. In addition, this outer end of each of the biasing members 52 and 54 is open, as at 56, so as to facilitate the at least partial collapse of the biasing members 52 and 54 when the converging flap structures 27' and 29' are forced into the open orientation by the positioning means 20 or 20' or by the medical instrument passing therethrough. As should be apparent, the separation of the converging flap structures 27' and 29' into an open position will force the biasing members 52 and 54 into an at least partially collapsed orientation (not shown) as they are sandwiched between the corresponding surfaces 13 and corresponding ones of the separated flaps 27' and 29'. An additional peripheral boundary 58 of each of the biasing members 52 and 54 may be integrally or otherwise fixedly secured to the exterior surface of the converging flaps 27' and 29' as clearly represented.

It is emphasized that the specific structural features, dimensions and configurations of each of the biasing members 52 and 54 may vary from that represented in FIGS. 9 through 13. However, the structure of the biasing members 52 and 54 as well as the material from which they are formed should be such as to confront the interior surface 13 of the trocar housing 12 in a manner which exerts an inwardly directed biasing force on the respective converging flaps 27' and 29' in order to normally bias the flaps 27' and 29', as well as the opening 31, in a closed and sealed orientation, in the absence of a laparoscopic or other medical instrument extending through the seal or valve structure 26'.

While exerting an appropriate biasing force on the converging flaps 27' and 29', the biasing members 52 and 54 are formed from a material having sufficient elasticity or flexibility to allow opening of the valve structure 26' and seal opening 31. Separation of the flaps 27' and 29' into an open orientation can be accomplished by passage of a laparoscopic or like medical instrument through the interior of the valve structure 26' as discussed in detail above with the embodiments of FIGS. 2-8. In addition and as clearly disclosed in FIGS. 9 and 13, the valve structure 26' may be disposed into the open orientation of FIG. 12 by manipulation of either of the preferred embodiments of the positioning device 20 or 20'.

Figure 12:
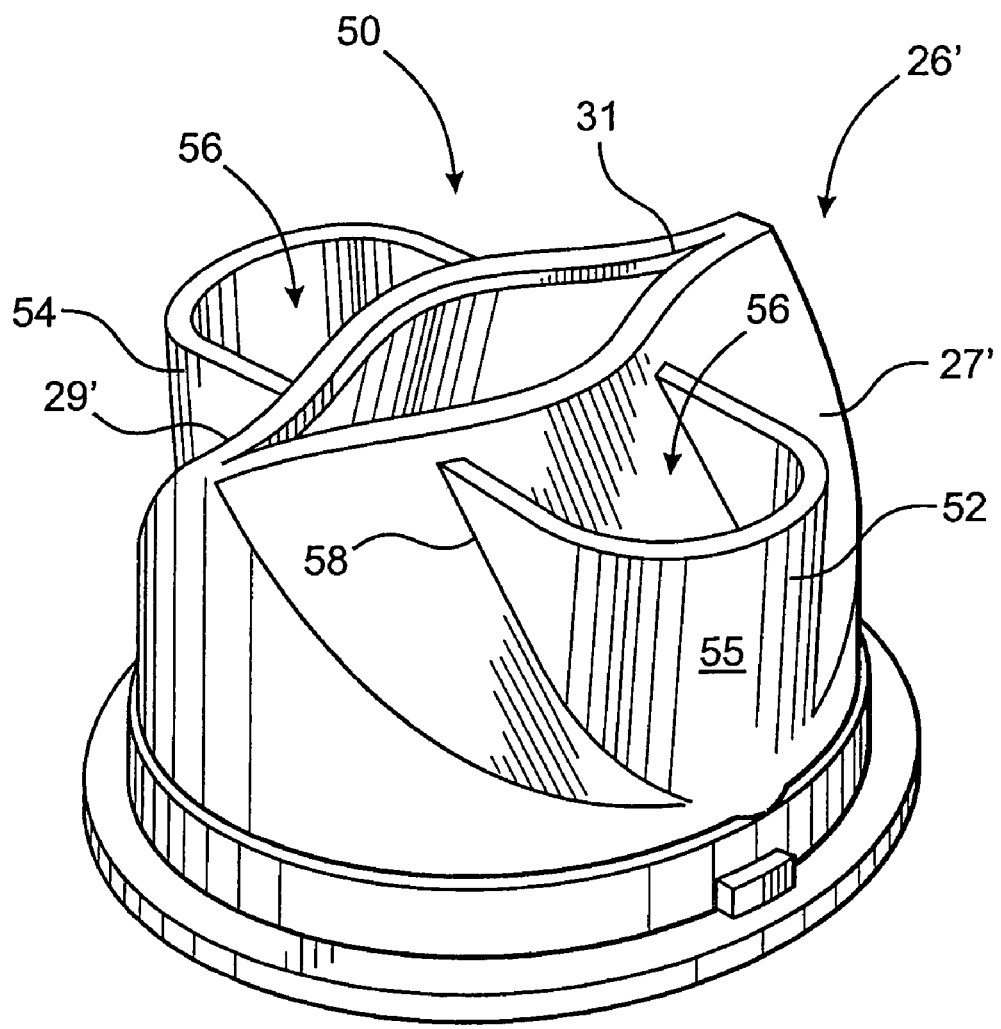
FIG. 12 is a perspective view of the preferred embodiment of the duckbill valve of the embodiment of FIGS. 9-11 in an open, unsealed orientation.
Figure 13A:
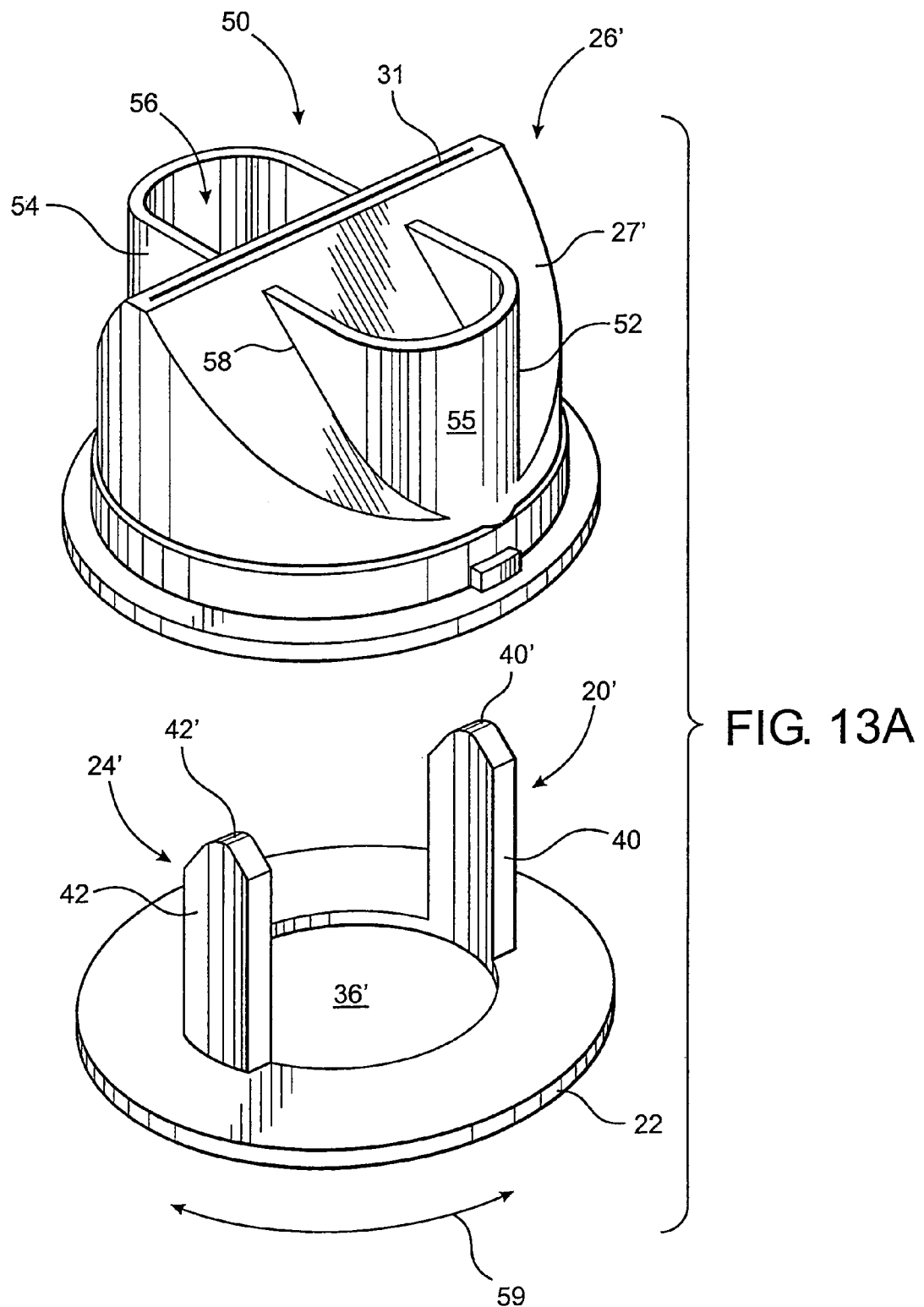
FIG. 13A is a perspective view in exploded form of the duckbill valve structure of the embodiments of FIGS. 9-12 as used with the different preferred embodiments of the positioning device as represented in FIGS. 6-8.
Figure 13B:
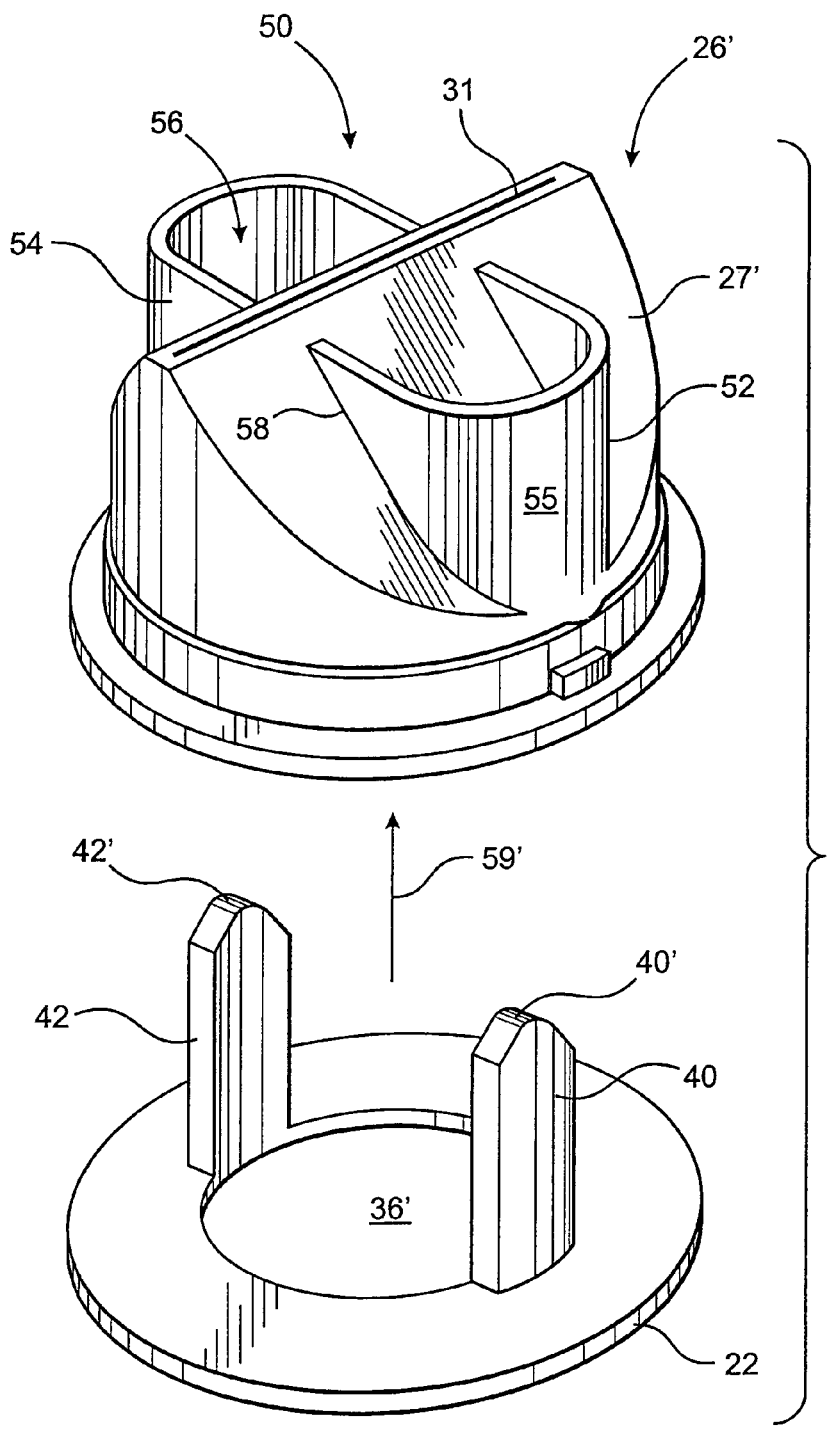
FIG. 13B is a perspective view in exploded form of the embodiment of FIG. 13A, wherein the positioning device is in a different, operative orientation.

As set forth in detail above relative to the descriptions of the embodiments of FIGS. 1-8, selective positioning and movement of the positioning devices 20 and 20' relative to the valve structure 26 and 26' will allow for the selective disposition of the valve structure 26 and 26' into the open orientation of FIG. 12 and/or the closed orientation of FIGS. 9 and 13. As also described in detail above, at least one preferred embodiment of the present invention defines this relative movement of the positioning device 20 and 20' as being rotational as indicated by directional arrows 59 and 60. As such, the positioning device 20 or 20' is mounted on the interior of the valve structure 26 or 26' and rotated therein to dispose the valve structure in either the open or closed orientation.

However, at least some of the various preferred embodiments of the present invention are not limited to such relative rotational movement. More specifically, and as at least partially and schematically demonstrated in FIGS. 9B and 13B, the positioning device 28 or 28' may be oriented in a generally 90 degree offset relation (or other relative orientation) relative to the orientation of the valve structure 26'. When so oriented, an axial or other appropriate directional movement, schematically indicated by 59' and 60', of the positioning device 20 and 20' into and relative to the valve structure 26' will force the flaps 27' and 29' into the open orientation as demonstrated in FIG. 12.

As with the previously described embodiments of FIGS. 1-8, the valve structure 26', when in the open position or orientation, thereby eliminates or significantly reduces contact or engagement of the flaps 27' and 29' with the exterior or other portions of a laparoscopic instrument passing therethrough. Normal frictional engagement between the converging flaps 27' and 29' is thereby eliminated. Accordingly, any anatomical specimen or object connected to the end of the laparoscopic instrument will not be inadvertently dislodged from the instrument, as it passes through the trocar 10, by engagement with the flap structures 27' and 29' or any other portion of the valve structure 26'. As also described above, each of the preferred embodiments of the present invention, including those of FIGS. 9 through 13, is also structured to accomplish a rapid desufflation or venting of the insuflation gas from the body cavity by selectively opening the seal or valve structure 26' when the positioning device 20 is in the open orientation.

Yet additional preferred embodiments of the present invention are represented in FIGS. 14A, 14B through 19A, 19B and while functionally similar to the previously described preferred embodiments these additional preferred embodiments are distinguishable there from. Such distinguishing features include the operative disposition of the positioning device on the exterior of the duckbill valve or like seal structure such that relative movement between the positioning device and the valve serves to selectively open and close the valve. Further, the exterior disposition of the positioning device relative to the valve still enables the valve to be selectively disposed into a seal open orientation and a seal closed orientation. Also, as set forth above, the seal open orientation may be at least partially defined by a forced engagement of the expander structure with predetermined portions of the seal structure so as to forcibly move the flaps of the duckbill valve outwardly, away from one another or otherwise open like valve or seal structures.

Therefore, with primary reference to FIGS. 14A, 14B and 15A, 15B, an additional preferred embodiment of the present invention includes a duckbill valve, generally indicated as 60, disposed within the interior of a trocar housing 12' and including flap structures 62 and 64. As with the previously described duckbill valves, the outer or distal end of the flaps 62 and 64 terminate in a valve opening 66 which is normally biased into a closed or sealed position as best shown in FIG. 14B. In addition, this preferred embodiment of the seal positioning assembly of the present invention includes a positioning device generally indicated as 68 including an expander structure located on the exterior of the valve 60 and also at least partially on the exterior of the valve housing 12'.

More specifically, the positioning device 68 includes an expander structure 70 comprising at least one but preferably a plurality, such as two, spaced apart expander members 72 and 74. Each of the expander members 72 and 74 include a spring-like mounting structure 76 formed from a material and/or being otherwise structured to have an inherent bias which normally disposes the contact members 78 in a "seal closed" orientation as demonstrated in FIGS. 14A and 14B. However, the exertion of an inwardly directed force on the biasing mounting members 76 will force the contact members 78 inwardly into forced engagement with predetermined portions of the exterior of the duckbill valve 60. This force will cause the flaps 62 and 64 to forcibly move outward into the open position as demonstrated in FIGS. 15A and 15B. The biasing material or structuring of the mounting member 76 will force the contact members 78 outwardly from the interior of the trocar housing 12' and out of the forced engagement with the predetermined portions of the duckbill valve 60 once the inwardly directed force on the mounting members 76 has been removed. The expander members 72 and 74 will then again assume the closed position demonstrated in FIGS. 14A and 14B.

For purposes of clarity, directional arrows 79 schematically represented in FIG. 14A represent the reciprocal movement of the expander members 72 and 74, as they are disposed between the seal open orientation and the seal closed orientation. Similarly, the schematic directional arrows 79' indicate the inwardly directed force exerted on the mounting member 76 of each of the expander members 72 and 74 in order to separate the flaps 62 and 64 of the duckbill valve 60 as clearly demonstrated in FIG. 15B. Other structural features associated with this preferred embodiment include the provision of O-ring or similar type sealing members 80 provided to prevent inadvertent escape or venting of the insufflation gas in the area of the contact member 78.

Yet another preferred embodiment of the seal positioning assembly of the present invention is demonstrated in FIGS. 16A, 16B and 17A, 17B respectively disclosing the duckbill valve or like seal structure 60 in a closed orientation and in an open orientation. In this preferred embodiment, the positioning device comprises an expander structure 82, including at least one but more preferably a plurality, such as at least two expander members 84 and 86. Each of the expander members 84 and 86 are mounted on the interior of the trocar housing 12" but exteriorly of the duckbill valve 60. Further, each of the expander members 84 and 86 may be integrally or otherwise fixedly secured to interior surface portions of the trocar housing 12" and are more specifically defined by curvilinear "ramps".

Figure 16B:
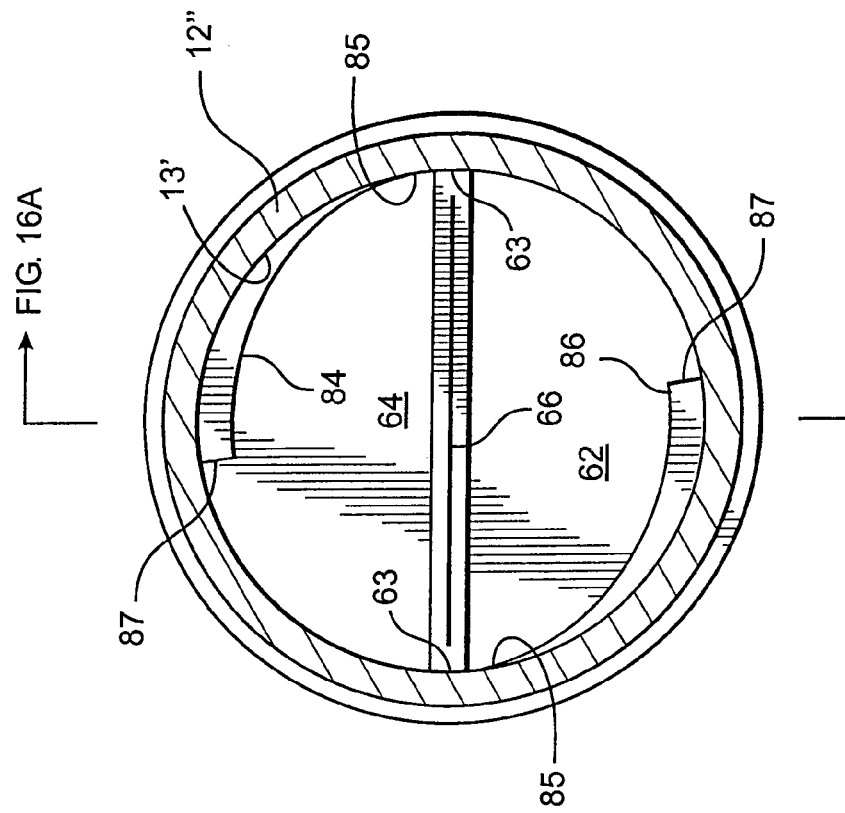
FIG. 16B is a cross sectional view of the embodiment of FIG. 16A taken along line 16B-16B.

As such, each of the ramp-like expander members 84 and 86 have an elongated, substantially curvilinear configuration which generally conforms to the curved shape of the interior surface 13' of the trocar housing 12". However, the structural configuration of each of the expander members 84 and 86 is such that they increase in width or lateral dimension from a first end 85 to a second end 87. As best shown in FIGS. 16B and 17B, this increased lateral dimension of each of the expander members 84 and 86 facilitates a greater extension thereof outwardly from the interior surface 13' and into the interior of the trocar housing 12" along their respective lengths from the first end 85 to the second end 87.

Figure 16A:
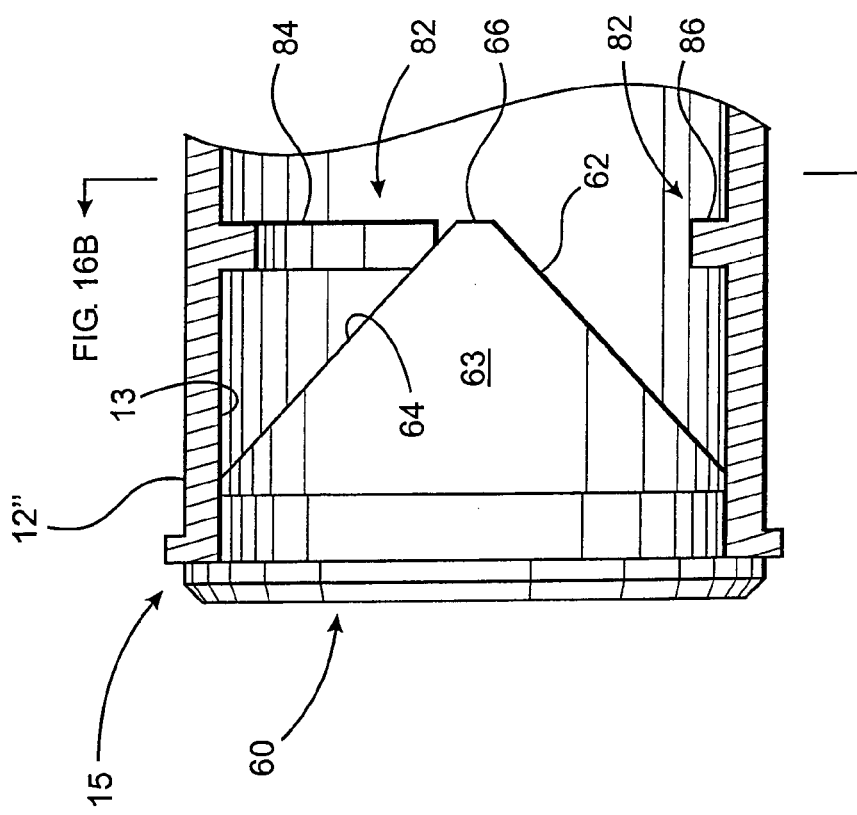
FIG. 16A is a cross sectional view in partial cutaway of yet another preferred embodiment of the seal positioning assembly of the present invention, as taken along line 16A-16A of FIG. 16B.

Therefore, the selective opening and closing of the duckbill valve 60 and more specifically the seal opening 66 is accomplished by rotation of the duckbill valve 60 within the interior of the trocar housing 12". Such rotation will cause predetermined exterior portions as at 63 to slidingly engage each of the oppositely disposed expander members 84 and 86. Moreover, as the width or lateral dimension of the expander members 84 and 86 increase between their first and second ends 85 and 87 respectively, the predetermined exterior portion 63 will be forcibly engaged by the expander members 84 and 86 causing a separation or outwardly forced movement of the flaps 62 and 64 and an opening of the seal opening 66 as clearly demonstrated in FIGS. 17A and 17B. The direction of rotation of the valve 60 relative to the trocar housing 12" and the positioning device 82 is dependant upon the orientation of the expander members 84 and 86. More specifically, an opening of the duckbill valve 60 will be accomplished as the predetermined portions 63 of the duckbill valve 60 move from the first end 85 towards the second end 87 of corresponding ones the expander members 84 and 86. As should be apparent, selective disposition of the duckbill valve 60 in the closed position of FIGS. 16A and 16B is accomplished by rotating the duckbill valve 60 in the opposite direction from that causing the opening of the duckbill valve 60.

An additional preferred embodiment of the seal positioning assembly of the present invention is represented in FIGS. 18A, 18B and 19A, 19B. The duckbill valve 60 is in its closed position in FIGS. 18A, 18B, and in its open position in FIGS. 19A and 19B. More specifically, as with the preferred embodiments of FIGS. 16A, 16B and 17A, 17B, the positioning device is located on the interior of the valve housing 12''', but exteriorly of the duckbill valve 60 and comprises the expander structure 90. Also somewhat similar in function to the embodiment of FIGS. 16 and 17, is the defining of at least one but preferably a plurality, such as two expander members 92 and 94 being generally structured to have a ramp-like configuration. The expander members 92 and 94 engage predetermined exterior portions 63 of the duckbill valve 60. However, differing from the previously noted embodiment, this preferred embodiment accomplishes a selective opening and closing of the duckbill valve by a linear and/or coaxial movement of the duckbill valve 60 within the trocar housing 12'''. With reference to FIGS. 18A and 19A, an external force in the direction represented schematically by arrow 91 will cause the predetermined exterior portion 63 of the duckbill valve 60 to movably engage the inwardly converging surfaces 92' and 94' of the expander members 92 and 94. Accordingly, from the closed position of FIG. 18B, the inwardly directed force 91 will cause a separation of the flaps 62 and 64 and an opening of the seal opening 66 as the respective expander members 92 and 94 forcibly engage the predetermined exterior portion 63 of the duckbill valve 60. Also, the dimension and configuration of the expander members 92 and 94 may vary in order to regulate the separation of the flap structures 62 and 64 and the size of the seal opening 66 when in its opened position of FIG. 19B.

It should be further noted that in each of the preferred embodiments of FIGS. 15A, 15B to 19A, 19B, the trocar housing 12', 12'', and 12''' is schematically represented. More specifically, in each of these embodiments it should be noted that the duckbill valve 60 or like seal structure would be completely enclosed within the trocar housing 12', 12'', and 12'''. Therefore, the open ended configuration as generally indicated as 15 in these various figures is for purposes of clarity only in describing the structural features of the positioning device and respectively associated expander structures and the relative movement between the respective positioning devices of these Figures and the duckbill valve 60 or like seal structure.

With further reference to the embodiments of FIGS. 16A, 16B through 19A, 19B, movement of the duckbill valve 60 relative to the trocar housing 12'' and 12''' as well as the respective positioning devices may be accomplished by any appropriate external structuring or mechanism capable of being mounted on and accessible from the exterior of the trocar housing 12'' and 12'''. Also, while not specifically represented, the biasing assembly 50 of the preferred embodiments of FIGS. 9A, 9B through 13A, 13B can be used with the duckbill valve 60 of the embodiments of FIGS. 14A, 14B through 19A, 19B.

It is again emphasized that while the seal or valve 26, 26' and 60 are represented as having a duckbill configuration, the various preferred embodiments of the seal positioning assembly of the present invention can be utilized with a variety of different types of seals or valves other than those having a duckbill configuration. Also, while the duckbill valves 26, 26' and 60 are represented as having only two opposing flaps, a "double duckbill" valve or other valve configuration may be utilized, which includes a number of flap structures other than two such as, but not limited to, four or more of such flaps or other sealing members. Accordingly, the positioning devices in the various preferred embodiments may include a different number of expander members other than two such as, but not limited to, four or more expander members. Further, the specific dimension and configuration of the different positioning devices disclosed in the accompanying Figures is at least partially dependent on the dimension, configuration and overall structure of the duckbill valves or other valve and seal structures with which the respective expander structures are utilized.

Since many modifications, variations and changes in detail can be made to the described preferred embodiment of the invention, it is intended that all matters in the foregoing description and shown in the accompanying drawings be interpreted as illustrative and not in a limiting sense. Thus, the scope of the invention should be determined by the appended claims and their legal equivalents.

Now that the invention has been described,

What is claimed is:

1. A seal positioning assembly for use with a trocar structured to open and close a seal structure having two opposing converging flaps, said seal structure defining an interior portion disposed between said opposing converging flaps, said seal positioning assembly comprising:
   a) a positioning device including base defining a central channel and an expander structure extending from said base, said positioning device disposed in communicating relation with the seal structure, said expander structure disposed within the interior portion of the seal structure,
   b) said expander structure disposable into a seal open orientation to open said seal structure by separation of said flaps and a seal closed orientation by rotational movement between said expander structure and the seal structure about a longitudinal axis of said channel, and
   c) said seal open orientation being at least partially defined by forced engagement of said expander structure with predetermined portions of the seal structure, wherein said seal structure is opened by rotation of said expander structure within said interior portion of said seal structure such that the expander structure forcibly engages interior surface portions of said opposing converging flaps.

2. A seal positioning assembly as recited in claim 1 wherein said expander structure comprises a plurality of expander members disposed in spaced relation to one another and collectively arranged to forcibly engage predetermined interior surface portions of the seal structure.

3. A seal positioning assembly as recited in claim 2 wherein said expander structure comprises at least two expander members disposed in spaced, substantially opposing relation to one another.

4. A seal positioning assembly as recited in claim 3 wherein each of said two expander members comprises a converging configuration extending from a proximal end to a distal end thereof.

5. A seal positioning assembly as recited in claim 3 wherein each of said two expander members comprises an elongated finger extending along an interior of the seal structure in spaced, substantially opposing relation to one another.

6. A seal positioning assembly for use with a trocar structured to orient a seal or valve into an open position and a closed position, said seal positioning assembly comprising:
   a) a seal structure having at least two opposing converging flaps and dimensioned and configured to be mounted within a trocar housing and disposed and structured to receive an instrument therethrough, said seal structure defining a proximal interior portion disposed between said opposing converging flaps,
   b) said seal structure including an opening disposed and structured to receive the instrument therethrough,
   c) a biasing assembly connected to said seal structure and disposed relative to the trocar housing to normally bias said seal structure and said opening into a closed position absent the presence of the instrument within said seal structure, and
   d) said biasing assembly comprising at least one biasing member connected to an exterior of said seal structure and including an open outer end, said one biasing member extending outwardly from said seal structure into confronting relation with an interior of the trocar housing, and
   e) an expander structure disposed within the interior portion of the seal structure, wherein said seal structure is opened by rotation of said expander structure within said interior portion of said seal structure such that the expander structure forcibly engages interior surface portions of said opposing converging flaps.

7. A seal positioning assembly as recited in claim 6 wherein said biasing assembly comprises a plurality of biasing members each having an open outer end and connected to an exterior of said seal structure, at least some of said biasing members disposed in confronting relation with an interior of the trocar housing.

8. A seal positioning assembly as recited in claim 6 further comprising an expander structure including at least two expander members, said two expander members extending outwardly from a base of said expander structure, said two expander members concurrently rotatable into a seal open orientation defined by outwardly forcing engagement with opposing interior surface portions of the seal structure.

9. A seal positioning assembly as recited in claim 8 wherein said two expander members are disposed in spaced, substantially opposing relation to one another.

\* \* \* \* \*